(12) United States Patent
Dadashian et al.

(10) Patent No.: US 10,682,519 B2
(45) Date of Patent: Jun. 16, 2020

(54) CONNECTOR FOR USE IN INJECTION MOLDED HEADER OF IMPLANTABLE PULSE GENERATOR

(71) Applicant: PACESETTER, INC., Sylmar, CA (US)

(72) Inventors: Asghar Dadashian, Porter Ranch, CA (US); Kavous Sahabi, Winnetka, CA (US); Avi Bilu, Pasadena, CA (US); Ofer Rosenzweig, Chatsworth, CA (US); Arees Garabed, North Hills, CA (US); Armando M. Cappa, Granada Hills, CA (US); Evan Sheldon, North Hollywood, CA (US); Xiangqun Chen, Santa Clara, CA (US); Alexander Robertson, Pasadena, CA (US)

(73) Assignee: PACESETTER, INC., Sylmar, CA (US)

( * ) Notice: Subject to any disclaimer, the term of this patent is extended or adjusted under 35 U.S.C. 154(b) by 137 days.

(21) Appl. No.: 15/177,229

(22) Filed: Jun. 8, 2016

(65) Prior Publication Data

US 2017/0354825 A1 Dec. 14, 2017

(51) Int. Cl.
| | |
|---|---|
| *A61N 1/00* | (2006.01) |
| *A61N 1/375* | (2006.01) |
| *H01R 24/58* | (2011.01) |
| *H01R 13/52* | (2006.01) |
| *H01R 13/187* | (2006.01) |
| *H01R 13/514* | (2006.01) |

(52) U.S. Cl.
CPC ......... *A61N 1/3752* (2013.01); *H01R 13/187* (2013.01); *H01R 13/5219* (2013.01); *H01R 24/58* (2013.01); *H01R 13/514* (2013.01); *H01R 13/521* (2013.01); *H01R 2201/12* (2013.01)

(58) Field of Classification Search
CPC ............... A61N 1/3752; A61N 1/3754; H01R 13/5219; H01R 13/187; H01R 13/54; H01R 13/521; H01R 24/58; H01R 2201/12
See application file for complete search history.

(56) References Cited

U.S. PATENT DOCUMENTS

2003/0163171 A1* 8/2003 Kast .................... A61N 1/3752
607/36
2011/0270330 A1* 11/2011 Janzig ................. H01R 13/187
607/2

* cited by examiner

*Primary Examiner* — Mallika D Fairchild
(74) *Attorney, Agent, or Firm* — Dean D. Small; The Small Patent Law Group, LLC

(57) ABSTRACT

A pulse generator comprises a header connector assembly coupled with a housing. The header connector assembly includes a connector assembly and a header enclosing the connector assembly. The connector assembly includes an electrically insulative segment, a first electrically conductive segment, and a second electrically conductive segment axially spaced apart from the first electrically conductive segment by the electrically insulative segment. Each electrically conductive segment includes a connector ring, a spring housing and a spring supported by the spring housing. The connector ring and spring housing are in electrical communication with each other. The electrically insulative segment includes an insulator ring that is positioned between the first and second electrically conductive segments. The insulator ring includes a first end and a second end axially opposite the first end. The first end includes a first recess that opens axially and receives therein a portion of the first electrically conductive segment.

26 Claims, 15 Drawing Sheets

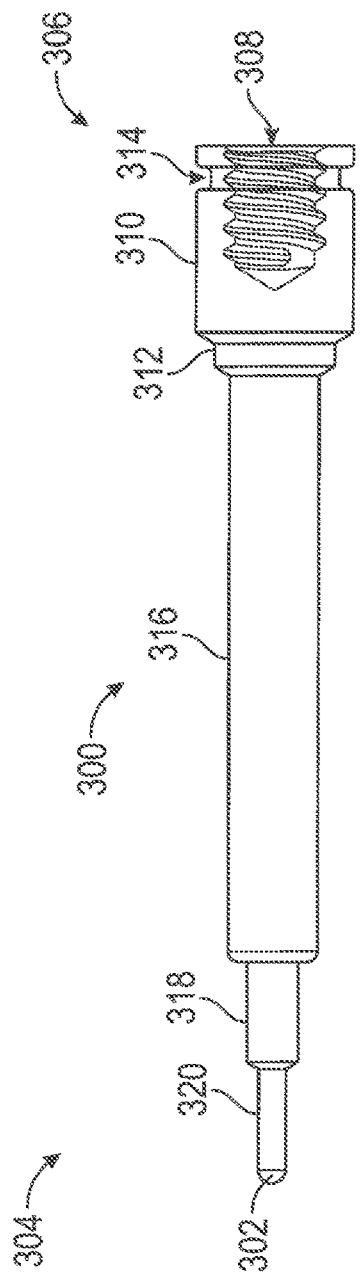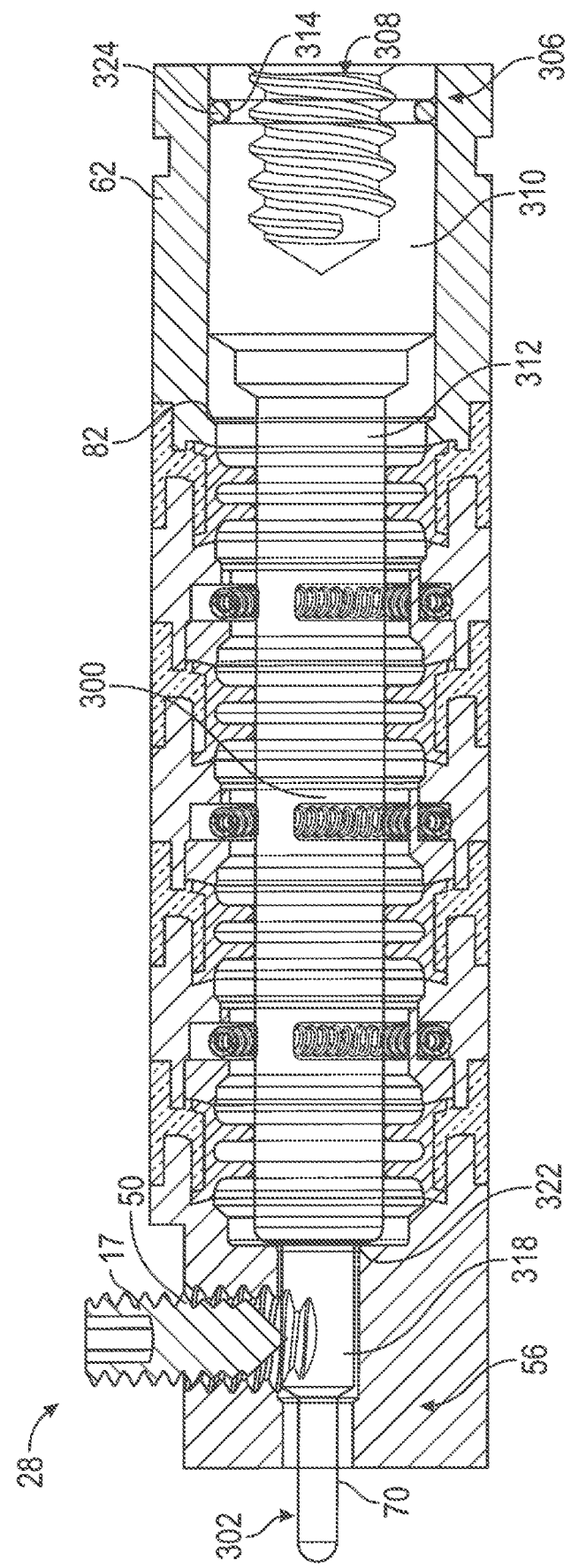

ND MOLDED HEADER OF IMPLANTABLE
CONNECTOR FOR USE IN INJECTION MOLDED HEADER OF IMPLANTABLE PULSE GENERATOR

TECHNICAL FIELD

Aspects of the present disclosure relate to medical apparatus and methods. More specifically, the present disclosure relates to a connector assembly for use in an injection molded header of an implantable pulse generator.

BACKGROUND

An Implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

Current header casting manufacturing processes and the associated methods of assembling the header and its enclosed connector assembly and electrical connection assembly onto the housing require multiple operations, are skill intensive, and unavoidably time consuming.

First, a header having cylindrical passages or openings generally matching the shape of a connector assembly is cast in epoxy. The header may have additional openings or passageways for electrically coupling the connector assemblies with a housing of an IPG. Second, the connector assemblies are positioned within the passages or openings of the pre-cast header. The openings are slightly larger than the connector assemblies so that the connector assemblies can be manually inserted into the openings. Third, electrical connections may be made (e.g., welding) between the connector assemblies and other components within the header that route the electrical signals between the connector assemblies and the housing. For example, an electrical connection assembly may be positioned within a particular opening or passage of the header such that it is in contact with the connections of the connection assemblies while protruding from an opposite end from the header so that it can be coupled with the feedthrus and into the header. Fourth, an overmolding process is done to securely affix the connector assemblies to the pre-cast header. More particularly, the overmolding process gap-fills the space between the openings in the pre-cast header and the inserted connector assemblies. The particular overmolding process may be injecting a thermosetting polymer (e.g., an epoxy) to a portion of the header to backfill the space between the openings and the connector assemblies. This overmolding or backfill process creates attachment and electrical sealing between the connector assemblies and the electrical connection assembly within the header. The backfill process is lengthy and expensive and may involve mold set-up, mold pre-heat, epoxy dispense, epoxy curing, and mold breakdown.

There is a need in the art for systems and methods that eliminate the backfill process. Additionally, there is a need in the art for connector assemblies that are suitable for injection molding of the header over the connector assemblies and electrical connector assembly.

BRIEF SUMMARY

The connector assembly disclosed herein allow for injection molding of the header over the connector assembly, which eliminates the need to pre-cast the header and eliminates the need for a backfill process.

Aspects of the present disclosure involve an implantable pulse generator for administering electrotherapy via an implantable lead. The pulse generator includes a housing and a header connector assembly configured to couple with the housing. The header connector assembly includes an outer portion and an inner portion. The outer portion includes a first connector ring, a second connector ring being at least substantially identical to the first connector ring, and an insulator ring positioned between the first and second connector rings. The inner portion includes a seal, a spring housing, and a spring supported by the spring housing. The insulator ring includes a body extending between a proximal end and a distal end. The proximal end of the body is differently shaped than the distal end.

In certain embodiments, the proximal end of the body of the insulator ring may include a proximal channel sandwiching a portion of the first connector ring within the proximal channel. The distal end of the body of the insulator ring may include a distal channel sandwiching a portion of the second connector ring within the distal channel.

In certain embodiments, the portion of the first connector ring is recessed from a first outer surface of the first connector ring and the portion of the second connector ring is recessed from a second outer surface of the second connector ring.

In certain embodiments, the insulator ring further may include an outer ring member including a proximal section and a distal section, a central member extending inward from the outer ring member, an inner proximal ring member extending proximally from the central ring member, and an inner distal ring member extending distally from the central ring member. The distal section of the outer ring member and the inner distal ring member may form the distal channel therebetween. The proximal section of the outer ring member and the inner proximal ring member may form the proximal channel therebetween.

In certain embodiments, a first distal-proximal thickness of the outer ring member is larger than a second distal-proximal thickness of the central ring member.

In certain embodiments, the inner distal ring extends further distally than the inner proximal ring extends proximally.

In certain embodiments, the distal channel is larger than the proximal channel.

In certain embodiments, the first and second connector rings are closest to each other at a point where the first connector ring is positioned in the proximal channel and the second connector ring is positioned in the distal channel.

In certain embodiments, the first connector ring may include a first body extending between a first proximal end and a first distal end. The first proximal end may be differently shaped than the first distal end. The second connector ring may include a second body extending between a second proximal end and a second distal end. The second proximal end may be differently shaped than the second distal end.

In certain embodiments, the first body may include a first outer ring member and a first distal ring member extending distally from the first outer ring member at the first distal end. The second body may include a second outer ring member and a second proximal ring member extending proximally from the second outer ring member at the second proximal end. The proximal end of the body of the insulator ring may include a proximal channel sandwiching the first distal ring member of the first connector ring within the distal channel. The distal end of the body of the Insulator ring may include a distal channel sandwiching the second proximal ring member of the second connector ring within the proximal channel.

In certain embodiments, the seal may include a seal distal end and a seal proximal end. The seal may be positioned between a second proximal surface of the second proximal end of the second body of the second connector ring at the seal distal end and a distal surface of the spring housing at the seal proximal end. The second proximal surface and the distal surface of the spring housing may be complementary to each other so as to oppose inward movement of the seal.

In certain embodiments, moving inwardly, the second proximal surface and the distal surface funnel towards each other.

Aspects of the present disclosure also include an implantable pulse generator for administering electrotherapy via an implantable lead. The pulse generator includes a housing and a header connector assembly configured to couple with the housing. The header connector assembly includes a connector assembly and a header enclosing the connector assembly. The connector assembly may include an outer portion and an inner portion. The outer portion may include a first insulator ring, a second insulator ring, and a connector ring positioned between the first and second insulator rings. The inner portion may include a seal, a spring housing, and a spring supported by the spring housing. The connector ring may include a body extending between a proximal end and a distal end, where the proximal end is differently shaped than the distal end. The body may include an outer ring member, a distal ring member recessed from and extending distally from the outer ring member at the distal end, and a proximal ring member recessed from and extending distally from the outer ring member at the proximal end.

In certain embodiments, the first insulator ring may include a first body extending between a first distal end and a first proximal end. The first distal end of the first body may include a distal channel sandwiching the proximal ring member within the distal channel.

In certain embodiments, the second insulator ring may include a second body extending between a second distal end and a second proximal end. The second proximal end of the second body may include a proximal channel sandwiching the distal ring member within the proximal channel.

In certain embodiments, the distal channel is differently shaped than the proximal channel.

In certain embodiments, the outer ring member extends between a distal planar step and a proximal planar step a first distance apart. The distal ring member may include a distal most surface and the proximal ring member may include a proximal most surface. A second distance extends between the distal most surface and the proximal most surface and the second distance may be greater than the first distance.

In certain embodiments, the body of the connector ring further may include a central member extending inwardly and between the distal ring member and the proximal ring member. The central member may include a proximal surface abutting a distal surface of the seal. The proximal surface may be configured and arranged to oppose inward movement of the seal.

In certain embodiments, the proximal surface is a conical surface that, moving inwardly, angles towards the seal to oppose the inward movement of the seal.

In certain embodiments, the spring housing may include another conical surface being a mirror image of the conical surface of the central member of the connector ring to aid in opposing inward movement of the seal.

Also disclosed herein is an implantable pulse generator for administering electrotherapy via an implantable lead. The pulse generator includes a housing and a header connector assembly. The header connector assembly is coupled with the housing and includes a connector assembly and a header enclosing the connector assembly. The connector assembly includes an electrically insulative segment, a first electrically conductive segment, and a second electrically conductive segment axially spaced apart from the first electrically conductive segment by the electrically insulative segment. Each electrically conductive segment includes a connector ring, a spring housing and a spring supported by the spring housing. The connector ring and spring housing are in electrical communication with each other. The electrically insulative segment includes an insulator ring that is positioned between the first and second electrically conductive segments. The insulator ring includes a first end and a second end axially opposite the first end. The first end includes a first recess that opens axially and receives therein a portion of the first electrically conductive segment While multiple embodiments are disclosed, still other embodiments of the present disclosure will become apparent to those skilled in the art from the following detailed description, which shows and describes illustrative embodiments of the disclosure. As will be realized, the various embodiments in this disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 14 is a side view of an alignment pin.

FIG. 15 is a side view of the alignment pin positioned within the connector assembly, shown in cross-section.

DETAILED DESCRIPTION

Implementations of the present disclosure involve an implantable pulse generator (IPG) for administering electrotherapy or other neurostimulation via an implantable lead having a lead connector end on a proximal end of the implantable lead. The IPG includes a housing or can and a connector assembly enclosed in a header, both of which are coupled to the housing or can. The header may include one or more connector assemblies. Each of the connector assembly includes a lead connector receiving bore or receptacle that includes electrical contacts that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

The IPG configurations and methods of assembly disclosed herein are advantageous for at least the reason that they eliminate the need for a pre-molded header and backfill process by providing a connector assembly suitable for injection molding the header around the connector assembly. The IPGs header and connector assembly may then be anchored to the housing via any process or mechanism known in the art.

The IPG configurations and methods of manufacture disclosed herein provide substantial cost and time savings over those IPG configurations and methods of assembly that are associated with the traditional pre-casting of the header, which requires a backfill process.

Before beginning a detailed discussion of a connector assembly suitable for use in an injection molding process of the header, a general discussion is first given regarding features of a common lead connector end at the proximal end of an implantable medical lead followed by a general discussion of the features of an IPG.

Figure 1:
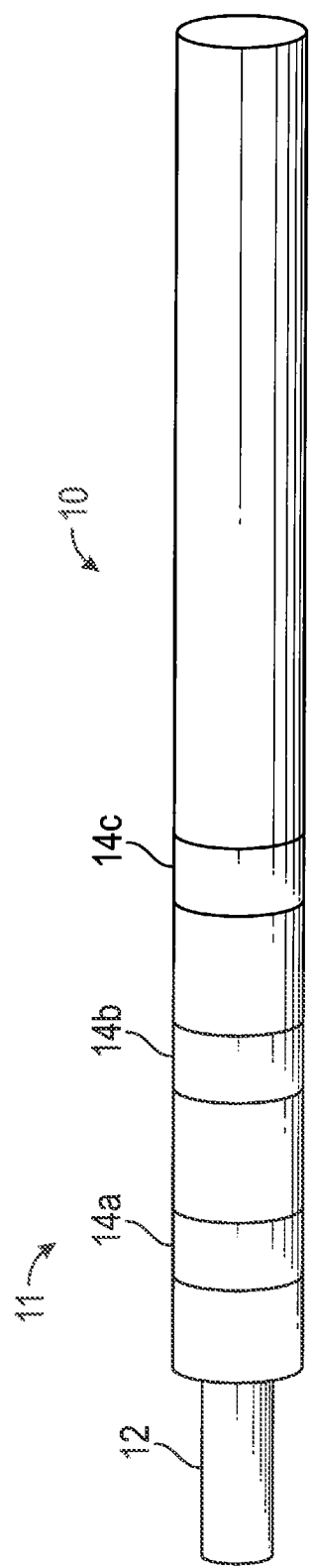
FIG. 1 is an isometric view of a proximal end portion (i.e., lead connector end) of a conventional quadripolar pacing lead conforming to the IS-4/DF-4 standards.

FIG. 1 shows a proximal end portion 10 of a conventional transvenous, quadripolar or IS-4 type pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. While the lead whose proximal end is shown in FIG. 1 is of the quadripolar or IS-4 variety, there are other leads with a different number of electrodes that may be generally represented by the lead in FIG. 1.

As is well known in the art, IS-4/DF-4 leads typically consists of a tubular housing of a biocompatible, biostable insulating material containing four conductor coils each surrounded by an insulating tube. One of the conductor coils is connected to a tip electrode at an end of the lead. The remaining three conductor coils are connected to annular ring electrodes, spaced-apart from each other, along the end portion of the lead. The four conductor coils are insulated from each other to electrically isolate the coils and, thus, prevent any internal electrical short circuit, while the housing protects the entire lead from the intrusion of body fluids. These insulating materials are typically either silicone rubber or polyurethane.

As seen in FIG. 1, the proximal lead end portion 10 includes a lead connector end 11 that conforms to the IS-4/DF-4 standard, comprising a three spaced-apart electrical ring terminals 14a, 14b, 14c and a tip terminal 12. Ring terminal 14a corresponds to the ventricular pace sense ring connection, ring terminal 14b corresponds to the right ventricle or RV coil connection, and ring terminal 14c corresponds to the superior vena cava or SVC coil connection. The tip terminal 12 corresponds to the ventricular pace sense tip electrode connection. The tip terminal 12 is electrically connected by means of one of the inner conductor coils to the tip electrode at the distal end of the lead. The ring terminals 14 are electrically connected to the three conductor coils contained within the tubular housing.

Figure 2:
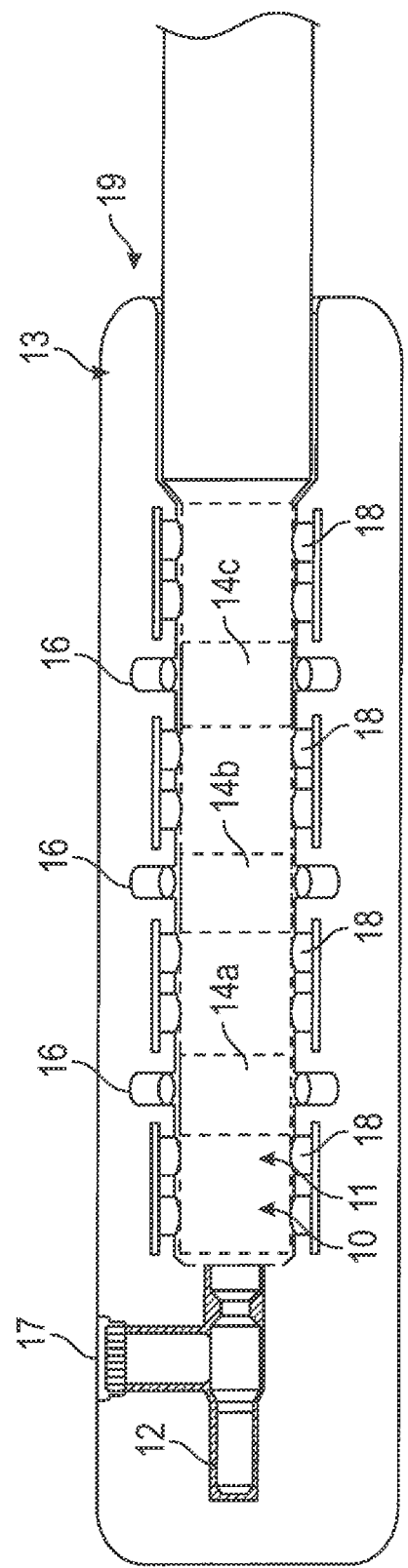
FIG. 2 is a side view of the proximal lead end portion of a lead positioned within a conventional connector assembly conforming to the IS-4/DF-4 standards.

As seen in FIG. 2, which is a side view of the proximal lead end portion 10 positioned within a conventional connector assembly 13 conforming to the IS-4/DF-4 standards, the ring terminals 14a, 14b, 14c of the lead connector end 11 may each be engaged by a conductive garter spring contact 16 or other resilient electrical contact element in a corresponding lead connector receiving bore of the header, the resilient electrical contact element being carried by the connector assembly 13 enclosed in the header as described below. The tip terminal 12 may be engaged by a conductive set screw 17.

The connector assembly 13 further includes spaced-apart seal rings 18 for abutting against in a fluid-sealing and electrically insulating manner the outer circumferential surface of the lead connector, thereby preventing body fluids from reaching the electrical terminals and contacts when the lead connector end 11 is plugged into the bore 19 of the connector assembly 13. With the lead connector end 11 of the lead inserted in the bore 19 of the connector assembly 13, the tip terminal 12 and ring terminals 14a, 14b, 14c are electrically coupled via the contacts 16, 17 of the connector assembly 13 and a feedthru to the electronic circuits within the hermetically sealed housing of the IPG (e.g., cardiac pacemaker, ICD, or other implantable tissue stimulation and/or sensing device such as those used in pain management, etc.).

Figure 3:
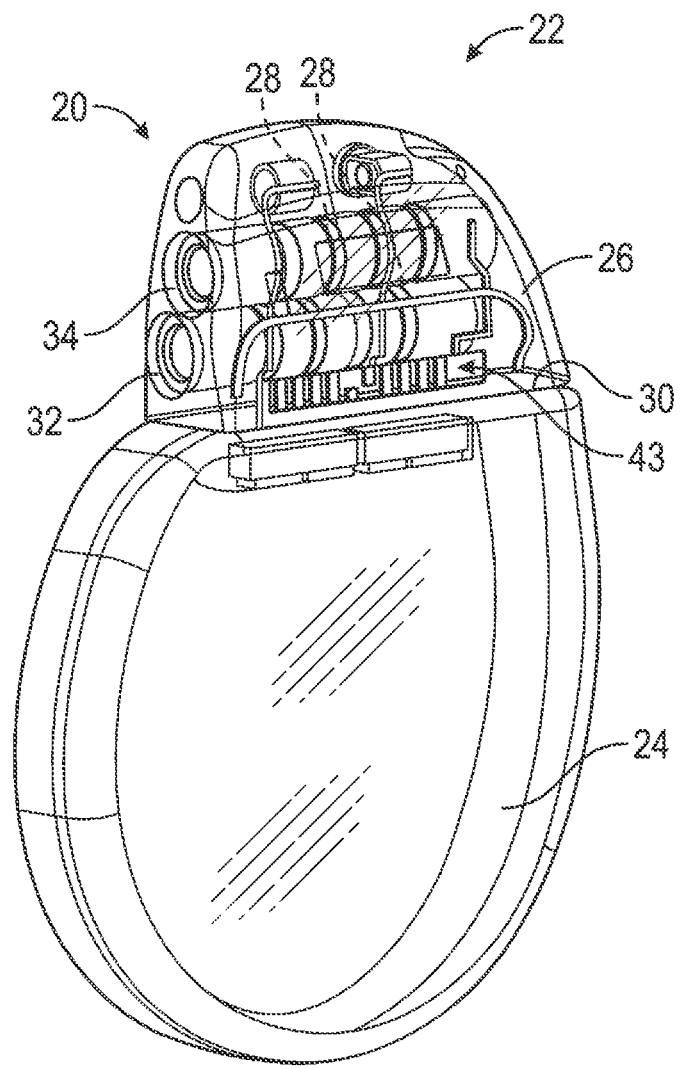
FIG. 3 is an isometric view of a cardiac pacemaker/defibrillator unit (i.e., implantable pulse generator (IPG)) having a header connector assembly and a housing.

FIG. 3 shows an isometric view of a cardiac pacemaker/defibrillator unit that is generally representative of any type of IPG 20 incorporating a header connector assembly 22 coupled to a housing 24. The header connector assembly 22 includes a header 26 enclosing a pair of connector assemblies 28. While the header connector assembly 22 shown in FIG. 3 depicts two connector assemblies 28, the header may include more or less connector assemblies 28 without departing from the teachings of the present disclosure. The IPG 20 includes a hermetically sealed housing 24, which is also known as a can or casing. The housing 24 encloses the electronic components of the IPG 20 with the header connector assembly 22 mounted along a top edge 30 of the housing 24.

FIG. 3 illustrates that, in some embodiments, the header 26 may include two connector assembly receiving bore or receptacles 32, 34 for receiving the connector assemblies 28, which will then receive the lead connector ends of two implantable leads. Other headers 26 may include more or less connector receiving bores 32, 34 as required by the particular IPG 20 requirements. For example, a particular IPG 20 utilizing a high voltage DF-4 connector may only require a single connector assembly receiving bore 32. The connector assembly 28 described herein is applicable to an IPG 20 having any number of connector assembly receiving bores without limitation.

Figure 4:
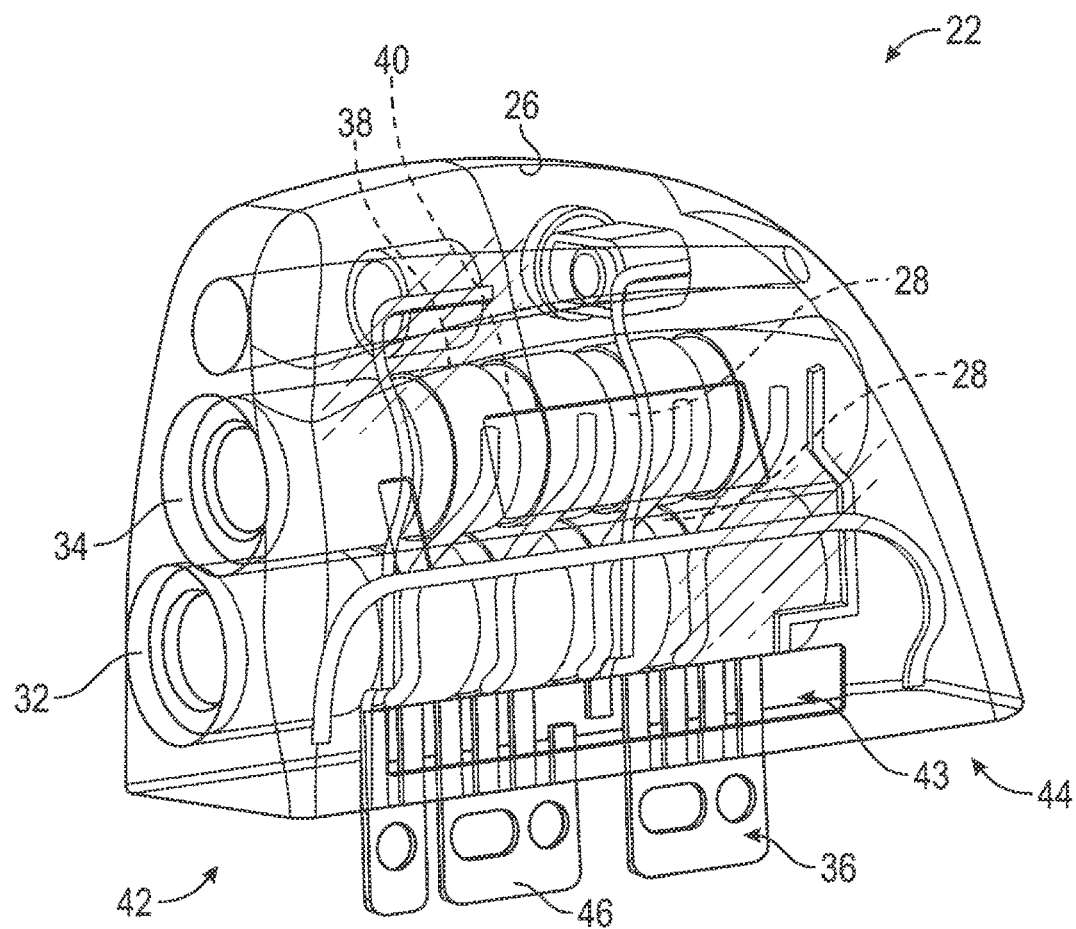
FIG. 4 is an isometric close-up view of the header connector assembly of FIG. 3

FIG. 4 is an isometric close-up view of the header 26 of FIG. 3. As seen in the figure, an electrical connection assembly 36 electrically connects between connector rings 38 of the connection assemblies 28 and the electrical componentry in the housing 24 (not shown in FIG. 4). More particularly, the electrical connection assembly 36 includes individual conductor ends 40 that contact (e.g., weld) the connector rings 38 of the connection assemblies 28. The electrical connection assembly 36 acts as the electrical feed through between the connector assemblies 28 and the can 24. As seen in FIG. 4, the header 26 includes an opening 42 on a bottom side 44 of the header 26 for the lower end 46 of the electrical connection assembly 36 to extend into the housing 24.

Figure 5:
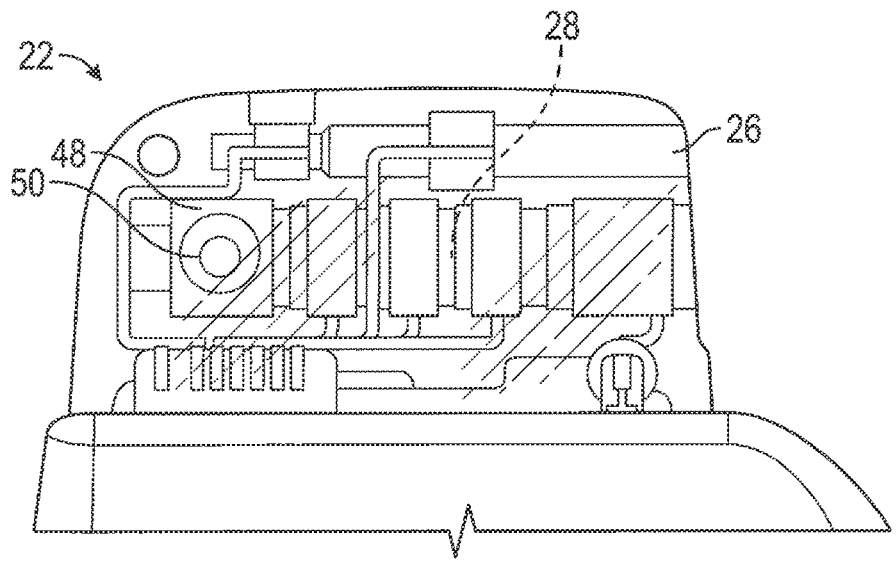
FIG. 5 is a side view of another embodiment of a header connection assembly.

FIG. 5 is another side view of a header connector assembly 22 having one connector assembly 28 within the header 26. As seen in the figure, the header 26 includes a set screw passage or receptacle 48 extending through the header 26. The set screw passage 48 aligns with a set screw bore 50 in the connector assembly 28. The set screw bore 50 may receive the set screw 17, described previously but not shown in FIG. 5, to electrically connect to the terminal tip 12 of the lead connector end 10 of the proximal end portion 11 of the lead.

Figure 6:
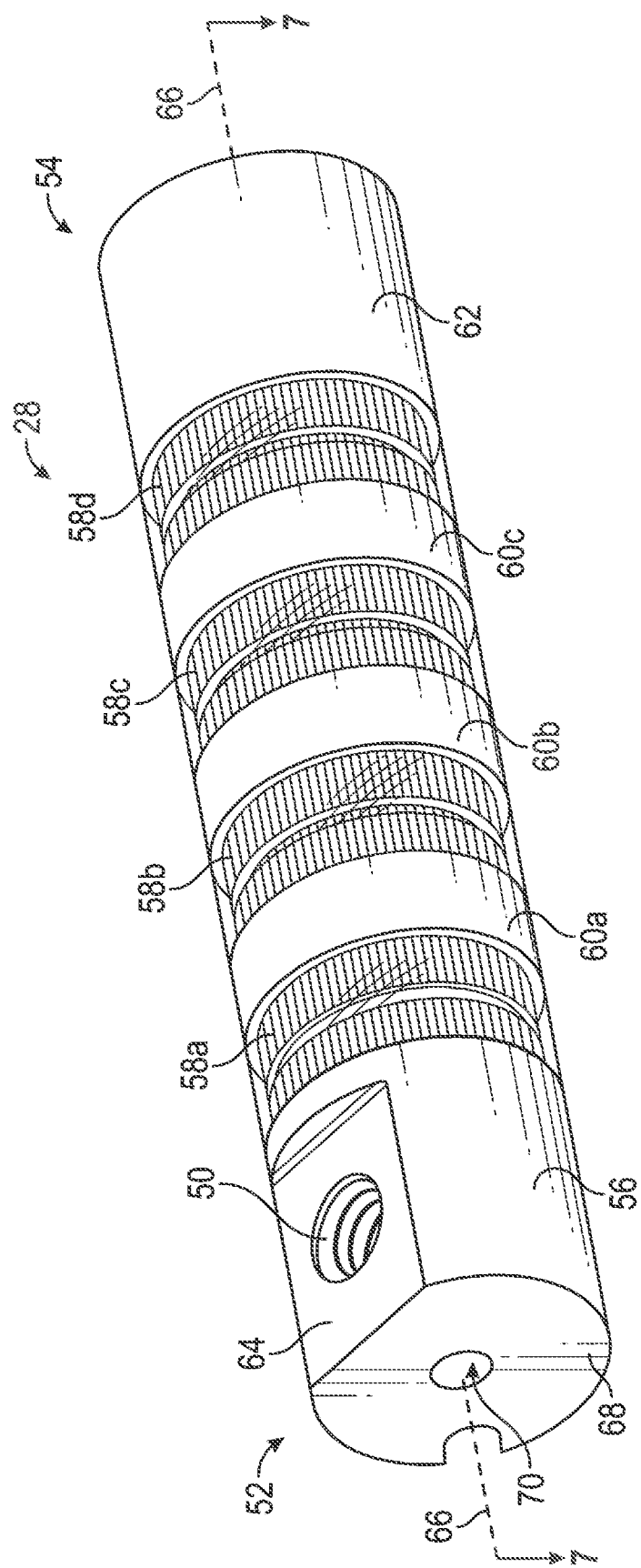
FIG. 6 is an isometric view of a representative connector assembly used with a header to form a header connector assembly.

Reference is made to FIG. 6, which depicts an isometric view of an embodiment of the connector assembly 28 that is suitable for injection molding of the header 26 (not shown in FIG. 6) around the connector assembly 28. As seen in FIG. 6, the connector assembly 28 extends along a longitudinal axis 66 between a distal end 52 and a proximal end 54, opposite the distal end 52. At the distal end 52 is a connector block 56, which may be made of steel. The connector block 56 includes the set screw bore 50, which is threaded to receive a set screw. Moving proximally from the connector block 56, the connector assembly 28 includes a first insulating ring 58a, a first connector ring 60a, a second insulating ring 58b, a second connector ring 60b, a third insulating ring 58c, a third connector ring 60c, and a fourth insulating ring 58d. At the proximal end 54 of the connector assembly 28 is an entrance ring 62, which may be made of steel.

The insulating rings 58a-d may be made from a reinforced polysulfone or similar material. The connector rings 60a-c may be made from steel. The outer surface of the connector assembly 28 is cylindrical with the connector block 56, the entrance ring 62, the insulating rings 58a-d, and the connector rings 60a-c having outer diameters that are about equal to each other, forming a generally uniform cylinder. The connector block 56 includes a planar, notched or recessed surface 64 that is about perpendicular from a planar distal surface 68. A terminal tip receiving bore 70 is centered on the planar distal surface 68 and extends into an inner opening within the connector assembly 28.

Conventional backfilling procedures and casting of the connector assembly 28 with the header 26 is done at atmospheric pressure. Thus, the stresses on the connector assembly 28 are minimal, as compared with an injection molding process where the header 22 is molded around the connector assembly 28. In an injection molding process, the connector assembly 28 may be subjected to pressures of about 20,000 pounds per square inch ("psi"). Conventional IS-4/DF-4 connector assemblies 28 are not designed to withstand such pressures. And, if conventional IS-4/DF-4 connector assemblies 28 were subjected to such pressures, a number of problems would likely occur. First, the insulating rings 58a-d, which typically have a low yield strength would likely deform or buckle under injection molding pressures. The deformed insulating rings 58a-d would allow the injected molten material (e.g., tecothane, pallethane) to leak inside the connector assembly 28, which would create bubbles in the molded header 26. The leakage into the connector assembly 28 may prevent electrical connections between the lead and the connector assembly 28 or may prevent insertion of the lead into the connector assembly 28, among other potential problems.

The connector assembly 28 described herein or, more particularly, the arrangement and configuration of the components of the connector assembly 28 is capable of withstanding the pressures subjected by the injection molding process of the header 26 around the connector assembly 28 and electrical connection assembly 36.

Figure 7:
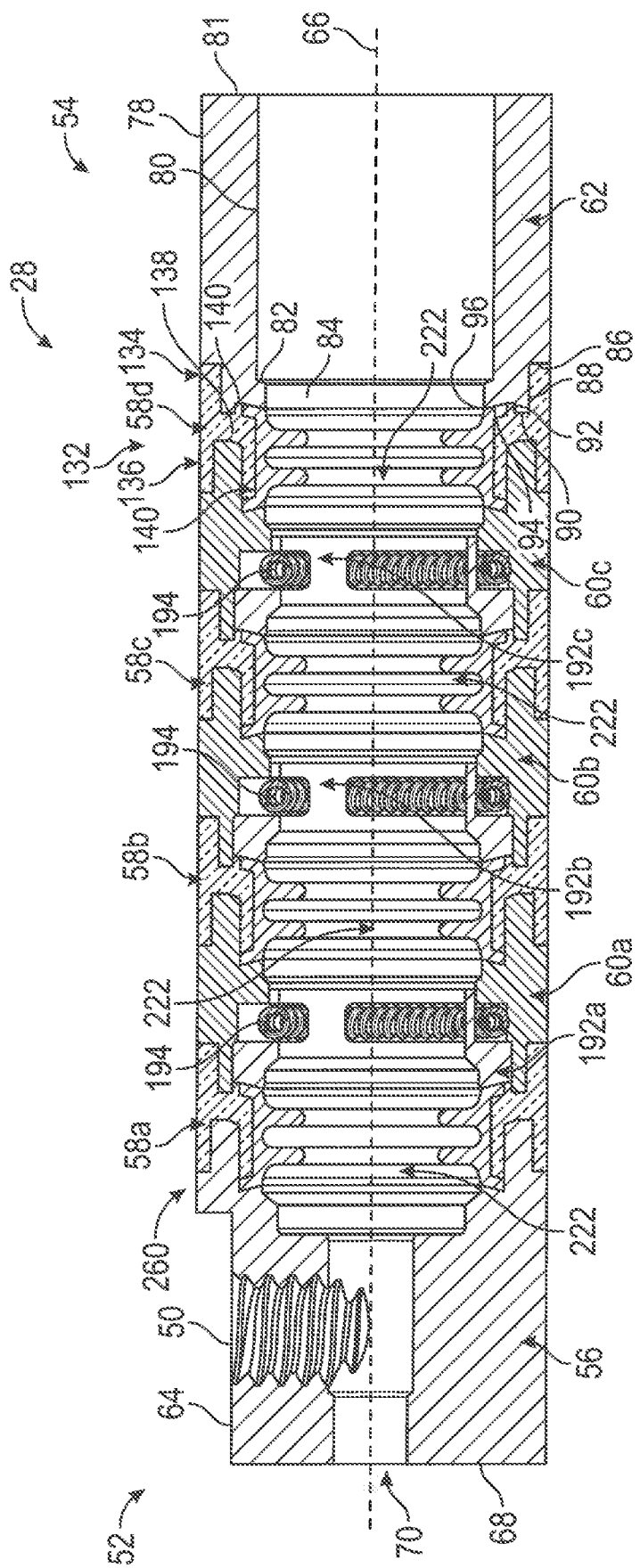
FIG. 7 is a cross-sectional side view of the connector assembly of FIG. 6.

To that end, reference is made to FIG. 7, which is a side cross-sectional view of the connector assembly 28 of the present disclosure with the sectional line taken along the longitudinal axis 66 of the connector assembly 28 and intersecting the set screw bore 50. As seen in FIG. 7, generally positioned radially inward from the insulating rings 58a-d and the connector rings 60a-c are three spring housings 192a, 192b, 192c each having a spring 194 positioned within the spring housing 192a-c. More particularly, the spring housings 192a-c abuttingly contact and are positioned inward of the connector rings 60a-c. Also positioned radially inward of the insulating rings 58a-d and the connector rings 60a-c are four double seal rings 222 which may be made of Silicone. More particularly, the double seal rings 222 abuttingly contact and are positioned inward of the insulating rings 58a-d. The spring housings 192a-c are each positioned between or sandwiched between the insulating rings 58a-d.

Each of the components of the connector assembly 28 will be discussed in turn. To begin, reference is made to FIGS. 7 and 12 for a discussion of the entrance ring 62. FIG. 7 is a side cross-sectional view of the connector assembly 28 and FIG. 12 is a close-up, side cross-sectional view of the entrance ring 62.

Figure 12:
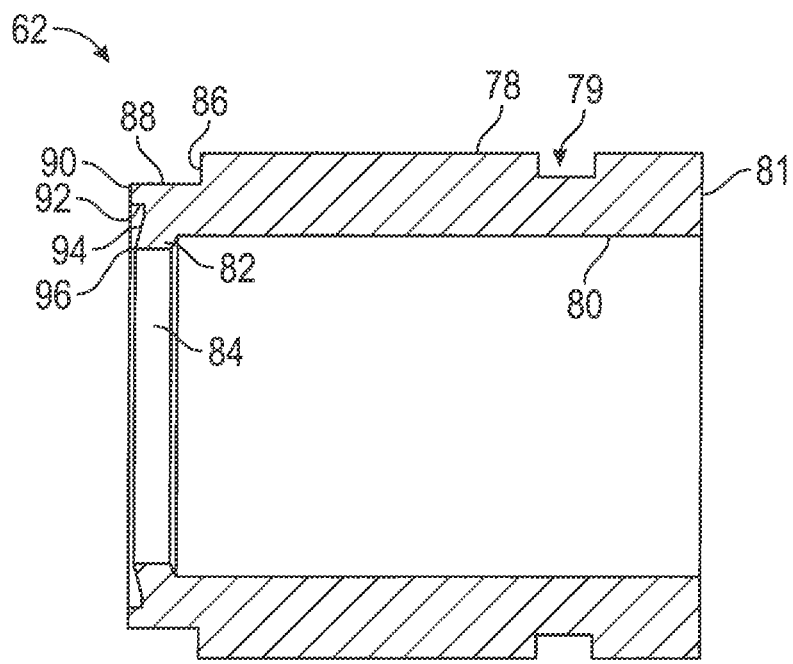
FIG. 12 is a cross-sectional side view of an entrance ring of the connector assembly of FIG. 6.

As seen in FIGS. 7 and 12, starting from the proximal end 54 of the connector assembly 28 and moving distally, an inner side of the entrance ring 62 includes a first proximal bore inner surface 80, a ramped transition surface 82, and a second proximal bore surface 84. The first and second proximal bore surfaces 80, 84 are cylindrical bores. The first proximal bore surface 80 includes an inner diameter that is greater than an inner diameter of the second proximal bore surface 84. The surfaces 80, 82, 84 of the entrance ring 62 are sized to receive a correspondingly shaped proximal end portion 10 of a conventional transvenous, quadripolar or IS-4 type pacing lead. The ramped transition surface 82 is sized to contact a corresponding surface of the pacing lead to prevent the pacing lead from extending further into the inner opening of the connector assembly 28.

Still referring to FIGS. 7 and 12, starting from the proximal end 54 of the connector assembly 28 and moving distally, an outer side of the entrance ring 62 includes a first proximal cylindrical outer surface 78 that includes a lock groove or recess 79 (not shown in FIG. 7) extending inward from the first proximal cylindrical surface 78. Distally of the first proximal cylindrical surface 78 is a first perpendicular planar step 86, a second proximal cylindrical surface 88, and a perpendicular planar edge or lip 90. The lip 90 includes a proximal extension surface 92 that is generally parallel to the second proximal cylindrical surface 88. Next, the entrance ring 62 includes a conical ramp surface 94 that extends distally and inward. The conical ramp surface 94 converges with the second proximal bore surface 84 at an inner bore edge 96. Referring back to the proximal end 54, a planar proximal surface 81 in the shape of a ring extends between the first proximal cylindrical outer surface 78 and the first proximal bore inner surface 80.

As seen in FIG. 7, the first perpendicular planar step 86, the second proximal cylindrical surface 88, the planar lip 90, the proximal extension surface 92 and the conical ramp surface 94 contacts a proximal portion of the insulator ring 58d and the double seal ring 222.

Figure 8:
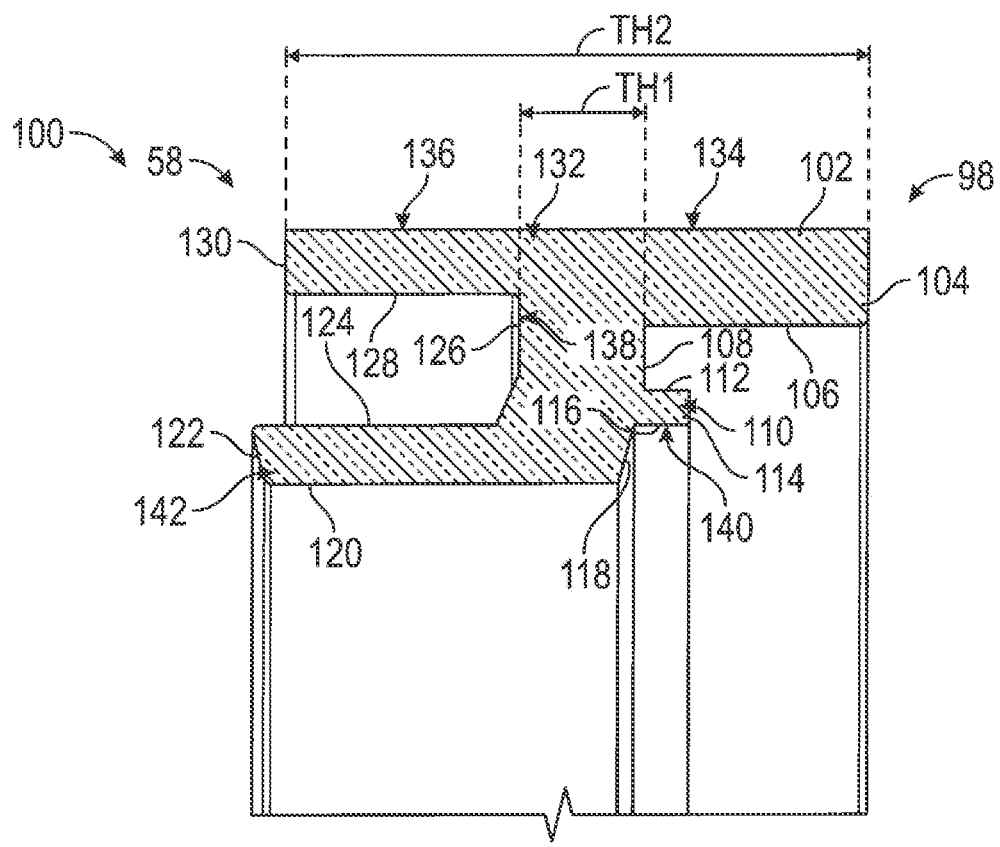
FIG. 8 is a cross-sectional side view of an insulator ring.

To best illustrate the geometry and configuration of the insulator rings 58a-d as it relates to the other components of the connector assembly 28, reference is made to FIG. 8, which is a close-up, cross-sectional view of a single insulator ring 58. As seen in the figure, the insulator ring 58 includes a body extending between a proximal end 98 and a distal end 100. Also, as seen in the figure, the proximal end 98 of the body is differently shaped than the distal end 100. A cylindrical outer surface 102 of the insulator ring 58 extends between the distal and proximal ends 100, 98. Generally, the insulator ring 58 includes a body having an outer ring member 132 having a proximal section 134 and a distal section 136. A central member 138 extends inward from the outer ring member 132 and is coupled with an inner proximal ring member 140 and an inner distal ring member 142. In this way, the insulator ring 58 may sandwich portions of the connector ring 60a-c, the connector ring 56, and the entrance ring 62. In particular, referring to the proximal end 54 of the connector assembly 28 in FIG. 7, and, in particular, the abutting nature of the entrance ring 62 and the insulator ring 58d, the proximal section 134 of the outer ring member 132 and the inner proximal ring member 140 sandwich the planar edge or lip 90 of the entrance ring 62.

The various surfaces of the Insulator ring 58 will be discussed by moving clockwise from the proximal end 98 of the outer surface 102 of the insulator ring 58. At the proximal end 98, the insulator ring 58 includes a proximal planar surface 104 on the proximal section 134 of the outer ring member 132 that is generally perpendicular to the outer surface 102. The proximal planar surface 104 transitions to a first proximal cylindrical surface 106 that extends distally and is generally parallel with the outer surface 102. The first proximal cylindrical surface 106 transitions to a proximal perpendicular step 108 of the central member 138 that extends inwardly. The proximal perpendicular step 108 transitions to a proximally extending flange or lip 110 of the inner proximal ring member 140 that includes an outer surface 112, a proximal surface 114, and an inner surface 116, where the outer and inner surfaces 112, 116 are generally parallel to each other. Extending inwardly from the inner surface 116 of the flange 110 is a distally inward extending conical ramp surface 118 that transitions to a distal cylindrical bore surface 120 of the inner distal ring member 142. The distal cylindrical bore surface 120 transitions at the distal end 100 of the insulator ring 58 to a distally outward extending conical ramp surface 122 that is generally a mirror of the distally inward extending conical ramp surface 118. The distally outward extending conical ramp surface 112 transitions to a proximally extending inner surface 124 of the inner distal ring member 142, which slopes to a first distal planar step 126 of the central member 138. The distal planar step 126 transitions to an inner distal surface 128 of the distal section 136 of the outer ring member 132 that extends distally and terminates at a second distal planar surface 130, which intersects the outer surface 102 of the distal end 100 of the insulator ring 58.

Generally, the inner distal ring member 142 extends further distally than the proximally extending lip 110 extends proximally.

As seen in the figure, the various surfaces on the distal end 100 of the insulator ring 58 or more particularly the distal section 136 of the outer ring member 132 and the inner distal ring member 142 form a distal channel therebetween for sandwiching an adjacent portion of a connector ring 60. And, the various surfaces of the proximal end 98 of the insulator ring 58 or more particularly the proximal section 134 of the outer ring member 132 and the inner proximal ring member 140 form a proximal channel therebetween for sandwiching an adjacent portion of the connector ring 60. Generally, the distal channel is larger and differently shaped than the proximal channel.

Figure 9:
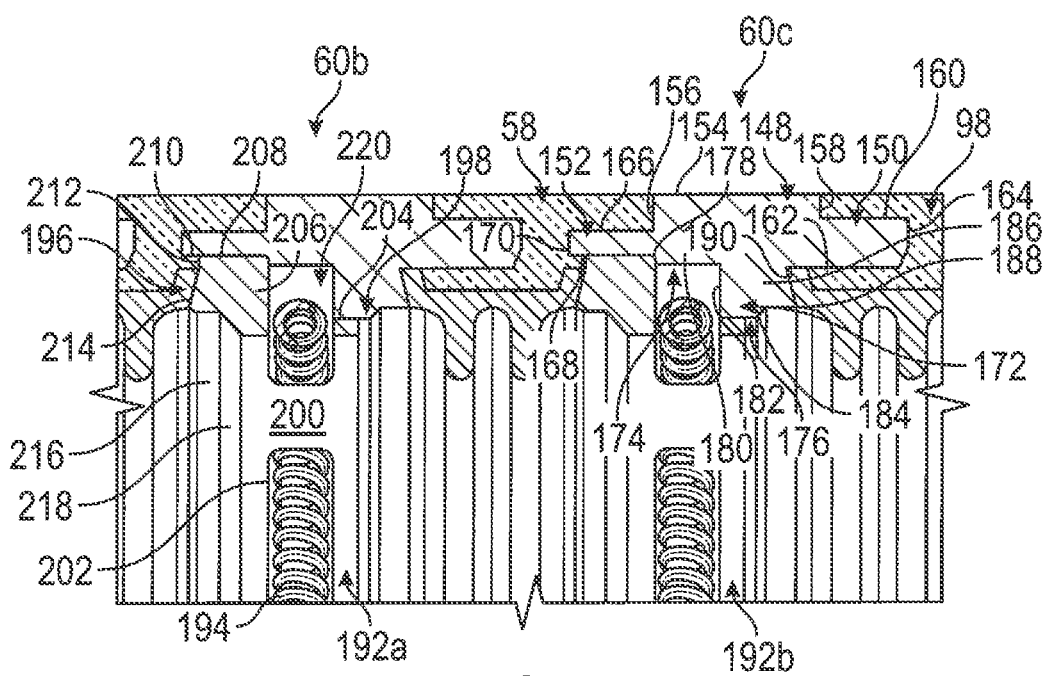
FIG. 9 is a close-up, cross-sectional side view of a portion of the connector assembly.

Reference is now made to FIGS. 7 and 9 for a discussion of the connector rings 60a-c. Each of the connector rings 60a-c includes a body extending between a proximal end 144 and a distal end 146. As seen in the figures, the proximal end of the body is differently shaped than the distal end of the body of the connector rings 60a-c. Generally, the connector rings 60a-c include an outer ring member 148, a proximal ring member or arm 150 that is recessed from the outer ring member 148, a distal ring member or arm 152 that is also recessed from the outer ring member 148, and a centrally extending member 172 on an inner end of the connector ring 60a-c.

The outer ring member 148 includes a cylindrical outer surface 154, a distal perpendicular planar step 156, and a proximal perpendicular planar step 158 opposite the distal perpendicular planar step 156. The distal and proximal perpendicular planar steps 156, 158 are generally parallel to each other. The proximal ring member 150 includes an outer cylindrical surface 160, an inner cylindrical bore surface 162, and a proximal surface 164 with a ramped section that extends between the outer cylindrical surface 160 and the inner cylindrical bore surface 162. The distal ring member 152 includes an outer cylindrical surface 166, an inner cylindrical surface 168, and a distal surface 170 that is planar and extends between the outer and inner cylindrical surfaces 166, 168. The centrally extending member 172 includes a distal section 174 and a proximal section 176. The distal section 174 includes a chamfered corner 178 at the intersection with the inner cylindrical surface 168 of the distal ring member 152. The chamfered corner 178 transitions to a recessed inner cylindrical surface 180. A distal inward extending surface 182 is adjacent the recessed inner cylindrical surface 180, which forms the distal most portion of the proximal section 176 of the centrally extending member 172. The distal inward extending surface 182 is planar and transitions at a generally perpendicular angle with an inner cylindrical bore surface 184. Moving counterclockwise, the inner cylindrical bore surface 184 transitions to an outwardly and proximally tapered conical bore surface 186, followed by a proximal cylindrical bore surface 188. The proximal cylindrical bore surface 188 transitions at an acute angle to a distally outward tapered conical surface 190, which transitions to the inner cylindrical bore surface 162 of the proximal ring member 150 at a rounded corner.

Still referring to FIG. 9, positioned inwardly of each connector ring 60a-c is a corresponding spring housing 192a-b supporting a contact spring 194. Each of the spring housings 192a-b is similarly shaped as follows. The spring housings 192a-b are ring shaped and include a distal section 196 and a proximal section 198. The proximal section 198 includes a cylindrical inner surface 200 having radially spaced-apart openings 202 extending from the inner surface 200 to a cylindrical outer surface 204 opposite the cylindrical inner surface 200. The distal section 196 of the spring housing 192a-c includes a proximal facing surface 206 that is generally perpendicular to the cylindrical outer surface 204. Moving distally from the proximal facing surface 206, the spring housing 192a-c Includes an outer cylindrical surface 208 that extends to distal edge 210. A distal planar step 212 extends generally perpendicular from the outer cylindrical surface 208, which then transitions to a distally and inwardly sloping conical surface 214. The sloping surface 214 transitions proximally to distal cylindrical surface 216 and then transitions to a proximally and inwardly sloping ramped or sloped surface 218 that meets with the cylindrical inner surface 200 of the proximal section 198 of the spring housing 192a-c.

As seen in FIG. 9, the proximal facing surface 206 of the distal section 196 and the cylindrical outer surface 204 of the proximal section 198 form a channel or receiving space 220 for the contact spring 194 to be housed within. The nature of the contact spring 194 is such that a portion of the spring will extend through the openings 202 in the proximal section 198 such that they will contact corresponding connections with the lead that is inserted into the connector assembly 28.

Figure 10:
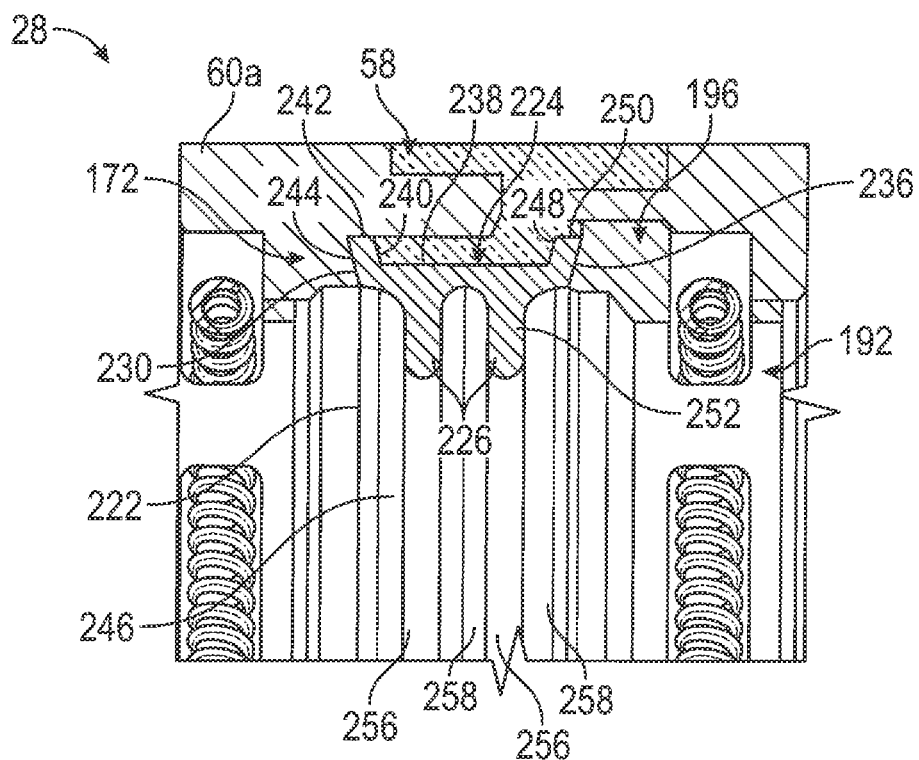
FIG. 10 is another close-up, cross-sectional side view of a portion of the connector assembly.

Reference is now made to FIG. 10, which is a close-up cross-sectional view of a portion of a connector assembly 28 showing a seal 222 positioned radially inward of an insulator ring 58 and sandwiched between the distal section 196 of the spring housing 192 and the centrally extending member 172 on an inner end of the connector ring 60a-c. As seen in the figure, seal 222 is configured as a double seal having an outer ring member 224 and a pair of radially inward projecting sealing members 226 that contact the lead when it is positioned within the connector assembly 28. The seal 222 may prevent bodily fluids, among other matter, from seeping between the seal 222 and the lead. The outer ring member includes a distal section having a distally and outwardly projecting member 230, a central cylindrical section having a cylindrical surface 238, and a proximal section having a proximally and outwardly projecting member 236 that is a mirror image of the distally and outwardly projecting member 230. The cylindrical surface 238 is recessed from the distal and proximally projecting members 230, 236. The distally projecting member 230 includes a proximal sloping surface 240 that slopes distally and outward. This surface 240 transitions to an outer cylindrical surface 242, which then transitions to a distal most sloping or conical surface 244 that slopes inward and proximally towards an inner surface 246 of the seal 222.

The proximally outward projecting member 236 of the proximal section includes a distal surface 248 that slopes proximally and outward from the cylindrical surface 238 of the central cylindrical section 232. The distal surface 248 then transitions to an outer cylindrical surface 250, which then transitions to a proximal most surface 252 that slopes inward and distally towards the inner surface 246 of the seal 222. The proximal most surface 252 may be conical and match, in mirror image fashion, the angle of the distal most sloping or conical surface 244 of the distally projecting member 230.

The inner surface 246 of the seal 222 is undulating or wavy and includes the pair of radially inward projecting sealing members 226 characterized by peak surfaces 256 and valleys 258, as seen in FIG. 10.

Figure 11:
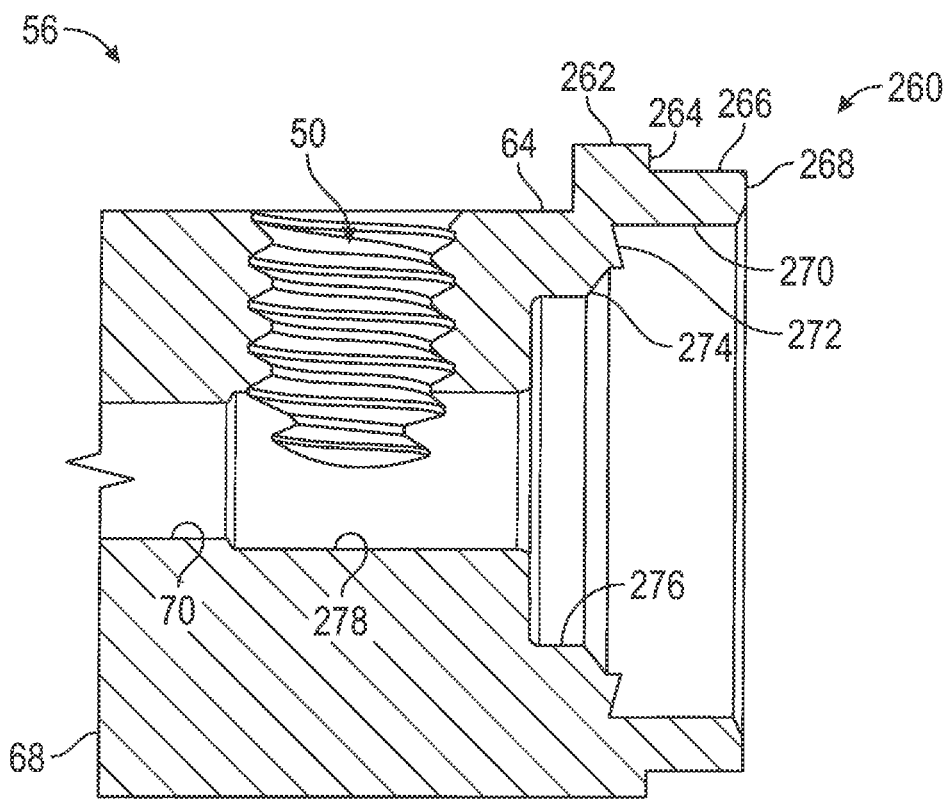
FIG. 11 is a cross-sectional side view of a connector block of the connector assembly of FIG. 6.

Reference is now made to FIGS. 7 and 11 for a discussion of the connector block 56 and its interaction with the seal 222 and insulator ring 58a. As seen in the figures, the connector block 56 includes the set screw bore 50, which is threaded to receive a set screw. The connector block 56 also includes the terminal tip receiving bore 70, which is centered on the planar distal surface 68 and extends into the inner opening within the connector assembly 28. Turning to the proximal end 260 of the connector block 56, it includes a surface geometry that matches the proximal end 144 of the connector rings 60a-c.

More particularly, as seen in FIG. 11, the proximal end 260 of the connector block 56 includes an outer cylindrical surface 262 that transitions into a proximal planar step 264 that is generally perpendicular to the outer cylindrical surface 262. The proximal planar step 264 transitions at a generally ninety degree angle to a proximal cylindrical surface 266. The proximal cylindrical surface 266 transitions to a proximal most planar surface 268, at a generally ninety degree angle. At an inward portion of the proximal most planar surface or edge 268, the surface 268 includes a rounded corner that transitions to a distally extending cylindrical inner surface 270 that is generally parallel to the proximal cylindrical surface 266. The proximal cylindrical surface 266, the proximal most planar surface 268, and the distally extending cylindrical inner surface 270 form a proximal ring member 280 that extends into the adjacent insulator ring 58a. The distally extending cylindrical inner surface 270 transitions at an acute angle to a proximally sloping or conical surface 272. The proximally sloping or conical surface 272 transitions to a distally extending and conically narrowing surface 274, which further transitions into an inner proximal cylindrical bore 276, which further transitions into a narrower central bore 278 and then the terminal tip receiving bore 70, which is narrower yet.

As can be seen in FIG. 7, the proximally sloping conical surface 272 abuts the distal most sloping or conical surface 244 that slopes inward and proximally towards the inner surface 246 of the seal 222. Because the distal and proximal conical surfaces 244, 252 of the seal 222 angle inward, when an inward force is exerted on the connector assembly 28 or, more particularly, the insulator rings 58a-d, the surfaces opposing the distal and proximal conical surfaces 244, 252 oppose the inward pressure and prevent failure of the insulator rings 58a-d and seals 222 during, for example, an injection molding process. More particularly, and in the case of insulator ring 58a that abuts the connector block, the proximally sloping conical surface 272 of the connector block 56 opposes the distal most sloping or conical surface 244 of the distally and outwardly projecting member 230 of the seal 222. And, on the opposite side of the seal 222, the proximal most conical surface 252 of the proximally and outwardly projecting member 236 of the seal 222 opposes the distally and inwardly sloping conical surface 214 of the distal section 196 of the spring housing 192.

As the seal 222 is forced inward from a force exerted on the insulator ring 58a, the seal 222 is forced into contact with the spring housing 192 at an angle relative to the applied force. Thus, the seal 222 is forced to try to "squeeze" through the opening formed between the inward most point between the spring housing 192 and the connector block 56 (or connector ring 60 for the seals 222 that are positioned inward of insulator rings 58b-c). Since the spring housings 192 are metal, they tend to resist the inward movement of the seal 222 as it is pushed via an outward force exerted on the insulator ring 58a. In this way, features of either of the connector block 56 and the spring housing 192, the connector rings 60a-b and the spring housings 192, or the connector ring 60c and the entrance ring 62 work in conjunction to exert an outward pressure against an inward pressure exerted on the insulator rings 58a-d and seal 222 from an injection molding process, for example.

In addition to the seal 222 being prevented from being forced inwardly from an outside force acting inwardly on the connector assembly 28, the insulator rings 58a-d are also suited for resisting an inward pressure exerted on it by an injection molding process, for example. Referring to FIG. 8, a thickness TH1 (in a distal-proximal direction) of the central member 138 of the insulator ring 58 defined between the proximal perpendicular step 108 and the distal planar step 126 may be about 0.02 inches. In certain embodiments, the thickness TH1 of the central member 138 may be about 0.01 inches. In certain embodiments, the thickness TH1 of the central member 138 may be about 0.03 inches. In certain embodiments, the thickness TH1 of the central member 138 may be about 0.04 inches. In certain embodiments, the thickness TH1 of the central member 138 may be within a range of about 0.01 to about 0.04 inches.

Also referring to FIG. 8, a thickness TH2 (in a distal-proximal direction) of the outer ring member 132 may be about 0.102 inches defined between the proximal planar surface 104 and the second distal planar surface 130. The thickness TH2 may also be the same as the length of the cylindrical outer surface 102 defined between the distal and proximal ends 100, 98 of the insulator ring 58. In certain embodiments, the thickness TH2 may be about 0.092 inches. In certain embodiments, the thickness TH2 may be about 0.112 inches. In certain embodiments, the thickness TH2 may be about 0.122 inches. In certain embodiments, the thickness TH2 may be about 0.132 inches. In certain embodiments, the thickness TH2 may be within a range of about 0.092 to about 0.132 inches. Accordingly, a ratio of the thicknesses of the central member 138 and the outer ring member 132 may be about 0.196 or 19.6 percent. Generally, the thickness TH2 is greater than the thickness TH1.

Because the thickness TH1 of the insulator ring 58 is the smallest at any point on the insulator ring 58, connector rings 60a-c positioned in the distal and proximal channels of the insulator ring 58 are also closest to each other at this point.

Accordingly, as seen in FIG. 9, utilizing an insulator ring 58 that sandwiches portions of the connector rings 60b-c and enables the connector rings 60b-c to be the thickness TH1 apart causes the insulator ring 58 to effectively prevent the insulator ring 58 from extending into the connector assembly 28 when subjected to the inward forces of the injection molding process.

Figure 13:
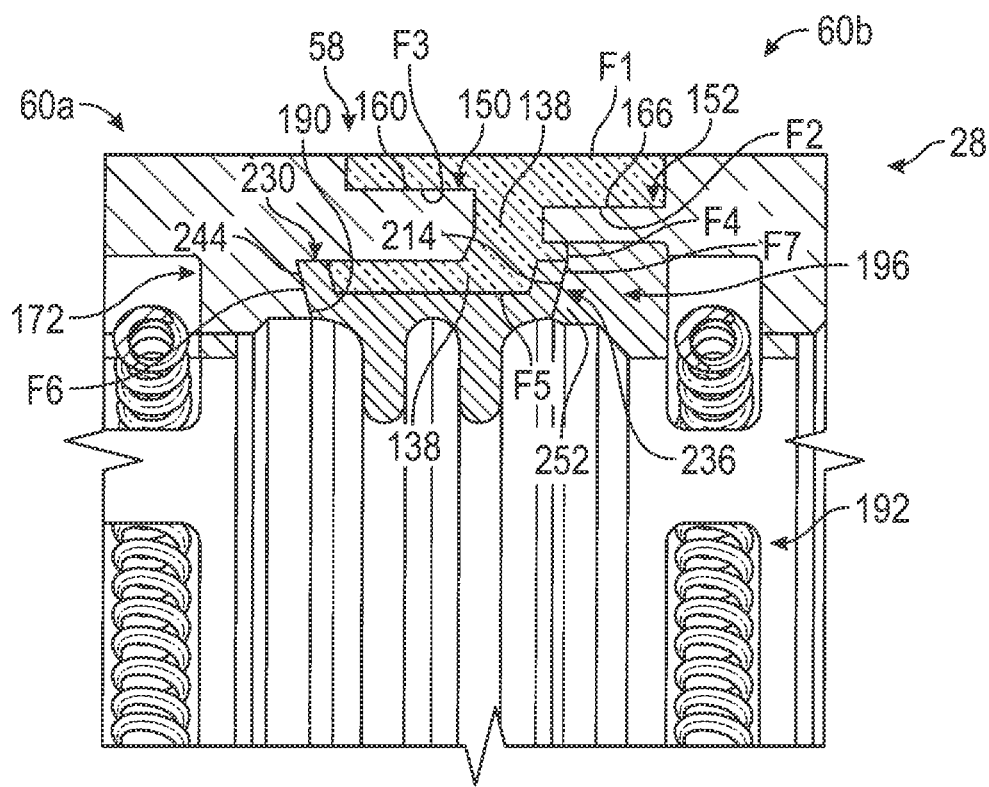
FIG. 13 is another close-up, cross-sectional side view of a portion of the connector assembly.

To further illustrate this point, reference is made to FIG. 13, which is a close-up cross-sectional view of a portion of the connector assembly 28 showing forces from an injection molding process and counteracting forces of the various elements of the connector assembly 28. As see in the figure, when an inward force F1 (i.e., a summation of forces acting inwardly on the outer surface of the connector assembly) is applied to the connector assembly, there are a number of corresponding forces acting against the force F1 to balance the forces. More particularly, the outer cylindrical surface 166 of the distal ring member 152 of the connector ring 60b exerts an outward force F2 to counteract a portion of the force F1 that is exerting inward pressure on the outer cylindrical surface 166. Also, the proximal cylindrical surface 160 of the proximal ring member 150 of the connector ring 60b exerts an outward force F3 to counteract a portion of the force F1 that is exerting inward pressure on the proximal cylindrical surface 160.

Still referring to FIG. 13, the outward most portion of the distal planar step 212 (shown in FIG. 9) on the distal section 196 of the spring housing 192, adjacent the distal edge 210 (also shown in FIG. 9), provides a counteracting force F4 against a portion of the force F1 exerted on it. Additionally, the seal 222 provides a counteracting force F5 by way of its own mechanical properties (e.g., stiffness) as the force F1 is transmitted through the central member 138 of the insulator ring 58. The seal 222 may be made of Silicone or a similar material, which is typically not sufficient on its own to counteract the forces F1 exerted though the insulator ring 58 by a process such as injection molding. Thus, the seal 222 described herein includes the distally and outwardly projecting conical member 230 at the distal section of the seal 222 and the proximally and outwardly projecting conical member 236 at the proximal section of the seal 222 to further resist inward moving of the seal 222 due to external forces (e.g., F1). And, as the force F1 urges the seal 222 inward, the distal most sloping conical surface 244 and the proximal most conical surface 252 of the seal 222 will contact corresponding surfaces of either: the connector block 56 and the spring housing 192; the connector rings 60a-b and the spring housings 192; or the connector ring 60c and the entrance ring 62 to resist the movement.

As seen in FIG. 13, the seal 222 is positioned between a connector ring 60a and a spring housing 192. Thus, the distal most sloping conical surface 244 of the seal 222 contacts the distally outward tapering surface 190 of the centrally extending member 172 of the connecting ring 60a, which exerts a force F6 against the seal 222 and, thus, a portion of the applied force F1. On the other side, the proximal most conical surface 252 of the seal 222 contacts the distally and inwardly sloping conical surface 214 of the distal section 196 of the spring housing 192, which exerts a force F7 against the seal 222 and, thus, a portion of the applied force F1.

During an injection molding process, the force F1 will, thus, be counteracted by the forces F1, F2, F3, F4, F5, F6, and F7, among others, as shown in FIG. 13.

Still referring to FIG. 13, another feature of the connector assembly 28 that makes it suitable for use in an injection molding process is the increased surface area contact between the insulator ring 58 and the connector rings 60a-b that is caused by having the connector rings 60a-b extend into the insulator ring 58. Stated differently, because the insulator ring 58 sandwiches portions of the connector rings 60a-b, the amount of surface area for sealing purposes is maximized as compared with an insulator ring and connector ring with a differing seal arrangement. For example, conventional connector rings and insulator rings do no sandwich each other; rather, they merely abut each other in planar contact. In such an orientation, relatively low yield strengths (e.g., far below 20,000 psi) may cause a compromise in the sealing between the connector ring and the insulator ring. Additionally, conventional insulator rings typically do not include a reduced thickness at an inner portion of the insulator ring to further prevent seepage of injection material through the seal and into the connector assembly.

Reference is now made to FIG. 14, which depicts a side view of an alignment pin 300. The alignment pin 300 is sized and shaped similar to the proximal lead end portion 10 of a lead connector end 11 that conforms to the IS-4/DF-4 standard, as shown in FIG. 1. The alignment pin 300 is used in the injection molding process by being positioned within the bore of the connector assembly 28, as seen in FIG. 15, to prevent injection molding material or gases from seeping into and damaging the internal components of the connector assembly 28. As seen in FIG. 14, the alignment pin 300 includes a distal tip 302 at a distal end 304 of the alignment pin 300. Opposite the distal end 302, a proximal end 306 of the alignment pin 300 includes a threaded bore 308 extending distally. Beginning from the proximal end 306 and moving distally, the alignment pin 300 includes cylindrical surfaces of progressively narrower diameters. In particular, the proximal end 306 includes a first cylindrical surface 310 and a second cylindrical surface 312 separated by a conical transitional surface. The first cylindrical surface 310 includes an O-ring groove 314 near the proximal most end. The second cylindrical surface 312 transitions via a conical transitional surface to a central cylindrical surface 316 that extends to a first distal cylindrical surface 318 and a second distal cylindrical surface 320. There is a planar proximal step 322 between the central cylindrical surface 316 and the first distal cylindrical surface 318.

Turning to FIG. 15, the alignment pin 300 is positioned within the bore of the connector assembly 28 such that the distal tip 302 extends out of the bore 70 of the connector block 56 for visual verification of full insertion of the alignment pin 300. In this position, the planar proximal step 322 abuts an inner wall of the connector block 56 and the conical transitional surface between the first and second cylindrical surface 310, 312 at the proximal end 306 of the alignment pin 300 abuts the of the ramped transition surface 82 of the entrance ring 62. As seen in the figure, an O-ring 324 is positioned within the O-ring groove 314 to aid in preventing seepage of injection molding material or gases into the bore of the connector assembly 28.

Once the alignment pin 300 is positioned within the bore of the connector assembly 28, the set screw 17 is threadably engaged with the set screw bore 50 until the tip of the set screw 17 contacts the first cylindrical surface 318 and prevents the alignment pin 300 from moving or being dislodged from within the bore of the connector assembly 28 during the injection molding process. The set screw 17 also acts as a barrier to limit or eliminate seepage of injection molding material from going into through the bore 50 and into the connector assembly 28.

After the injection molding process is complete, another pin (not shown) having a threaded distal tip may be threadably engaged with the threaded bore 308 of the alignment pin and then urged or forced proximally to withdraw the alignment pin 300 from the connector assembly 28 (i.e., after the set screw 17 is removed from the bore 50).

Figure 16:
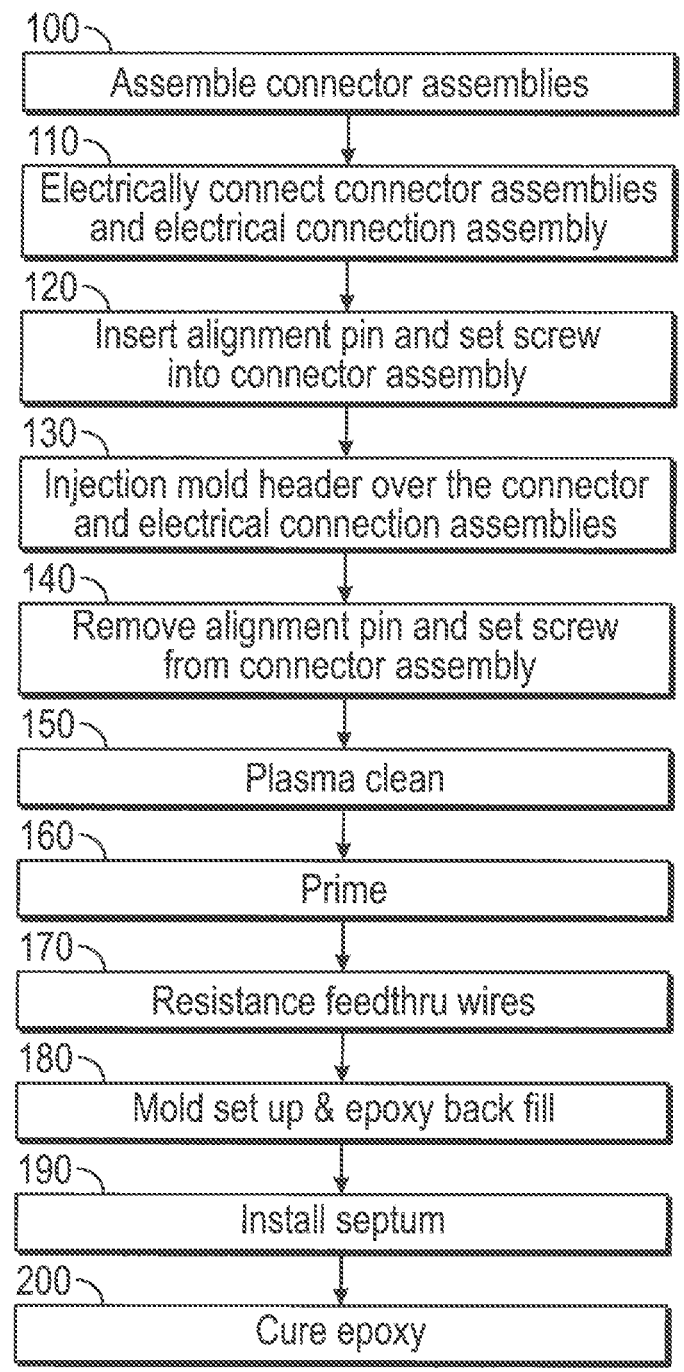
FIG. 16 is a flowchart depicting a method of manufacturing of an implantable pulse generator via an injection molding process.

As can be understood from FIG. 16, which is a flow chart illustrating a method 400 of manufacturing the IPG 20, the connector assemblies 28 are assembled [block 100]. The connector assemblies 28 are then electrically coupled via ribbon welding to the electrical connection assembly 36 [block 110]. It is noted that providing the electrical connections at this stage of the process is more efficient as compared with welding through a weld-window in a pre-molded or cast header 26. Next, the alignment pins 300 are inserted into the connector assemblies 28 and the set screw 17 is threadably engaged with the set screw bore 50 [block 120]. The header 26 is injection molded around the connector assemblies 28 and the electrical connection assembly 36 to form the header connection assembly 22 [block 130] and the set screw 17 and alignment pins 300 are removed from the connector assemblies 28 [block 140]. In one embodiment, the polymer of the injection molding may be polyurethane, tecothane, pellethane, or bionate, among others. While the alignment pins 300 are removed at block 140, the pins 300 may be moved at another step in the process without limitation.

The header connection assembly 22 is plasma cleaned [block 150], primed [block 160], and then the header connection assembly 22 is electrically connected to the housing 24 by resistance welding [block 170]. It is noted that the header connection assembly 22 may be molded with a side opening 43, as seen in FIGS. 3 and 4, to provide access to the various electrical components of the electrical connection assembly 36 positioned within the header 26. A next step in the manufacturing process may include setting up a mold and epoxy backfilling the side opening 43 [block 180]. Septums (not shown) are installed over the setscrews used to secure lead connector ends to the connector assemblies 28 [block 190]. The epoxy is then cured [block 200].

The process described in FIG. 16 may eliminate various steps in an alternative process that employs a pre-molded header. For example, when pre-molding a header, the two connector assembly receiving bore or receptacles 32, 34, as seen in FIGS. 3 and 4 of the present IPG 20, must be molded larger than the connector assemblies 28 so that the connector assemblies can be inserted into the bores 32, 34 after the header is molded. And, if the connector assemblies 28 are inserted into the pre-molded header, there must be a large window or opening (above the side opening 43, in FIG. 3) so that the connector assemblies 28 can be resistance welded to the leads of the electrical connection assembly 36. Welding within this window is time intensive and costly due to its complexity and required skill of the welder.

Once the connector assemblies 28 are welded to the electrical connection assembly 36, the large window and the extra space in the bores 32, 34 surrounding the connector assemblies 28 must be backfilled with epoxy and cured. A common cause for rework involves epoxy entering the connector assembly bores during this backfill process. When the epoxy enters the connector assembly bores, critical electrical connections are often compromised. The rework for these issues is often time intensive and increases manufacturing costs.

Injection molding the header 26 over the connector assemblies 28 and electrical connection assembly 36, as illustrated in FIG. 16, encapsulates the connector rings 601-c of the connector assemblies 28 with high pressure injected material. Thus, the electrical connections are more secure than with a conventional backfill process. More generally, injection molding the header 26 over the connector assemblies 28 ensures the assemblies 28 will maintain proper alignment along their axes, whereas in a backfill process there is more variability and more possibility for inaccurate alignment of the connector assemblies 28.

As discussed above and further in view of additional embodiments discussed below, the connector assembly 28 via its reinforcing of the insulator rings 58a-58d with portions of adjacent metal structures, such as, for example, the connector rings 60a-60, the spring housings 192a-192c, the connector block 56 and/or the entrance ring 62, is configured such that the connector assembly 28 can be subjected to the high pressures associated with injection molding when the header is injection molded about the connector assembly and without leakage of the injected material into the confines of the connector assembly.

Figure 17:
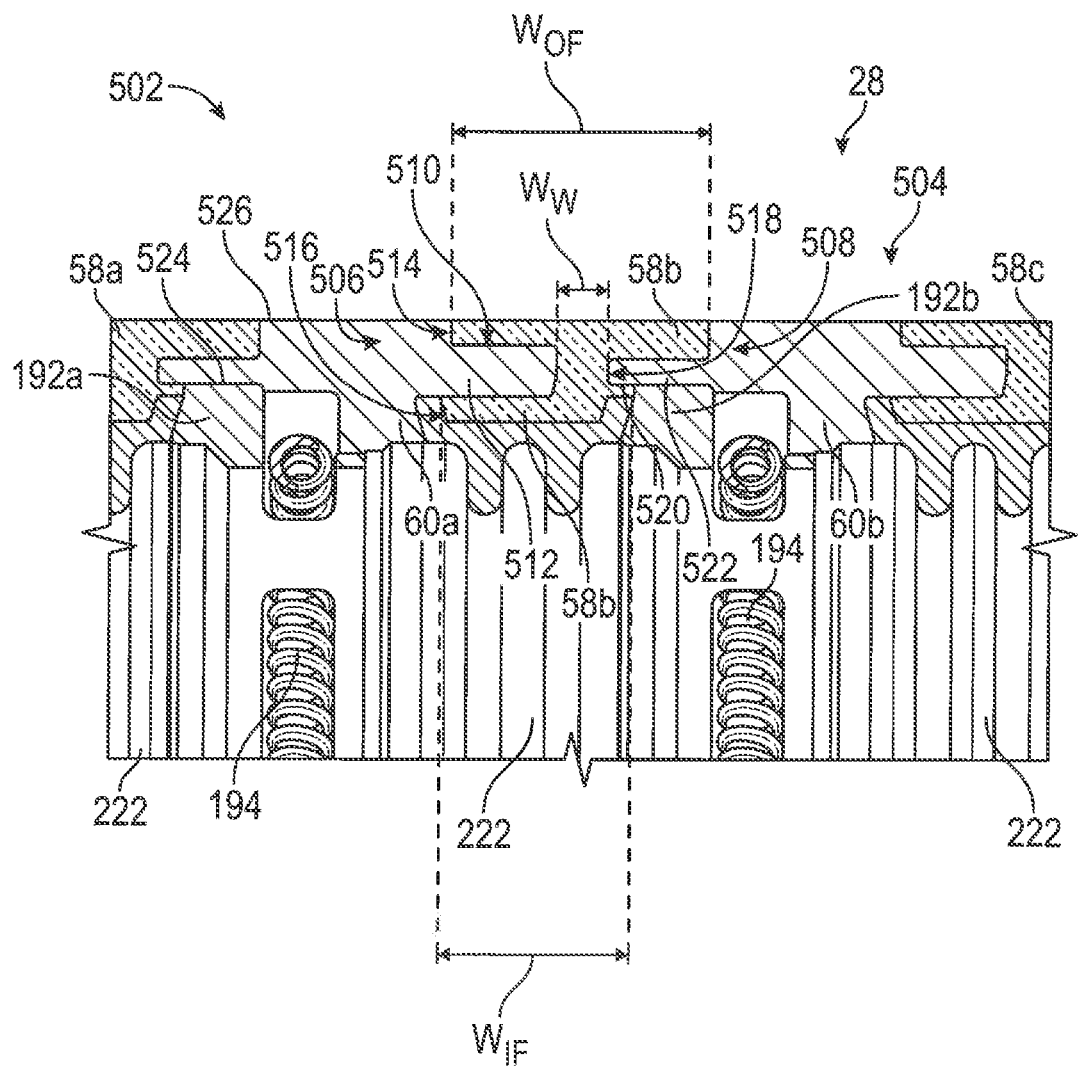
FIG. 17 is the same view as FIG. 9 and reflects a first embodiment of the reinforcement of the insulator rings as already discussed in detail with respect to FIGS. 6-15.
Figure 18:
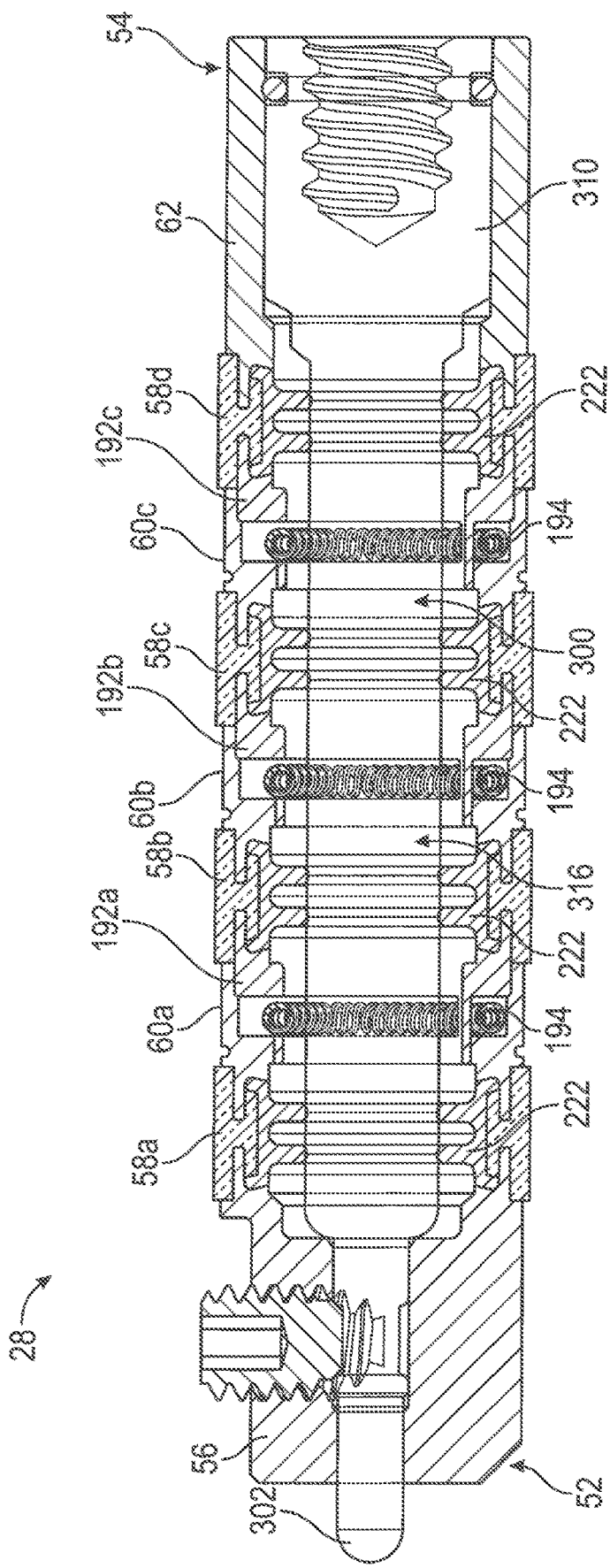
FIG. 18 is a view similar to that of FIG. 7, except reflecting a second embodiment of the reinforcement of the insulator rings.
Figure 19:
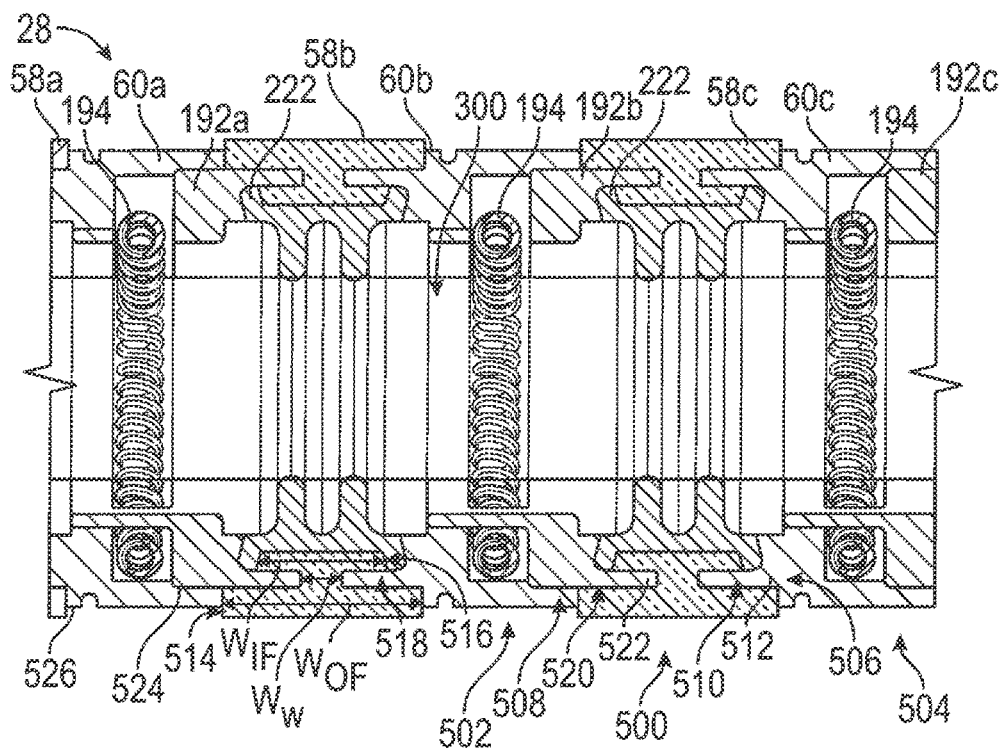
FIG. 19 is an enlarged view of a central portion of the connector assembly depicted in FIG. 18.
Figure 20:
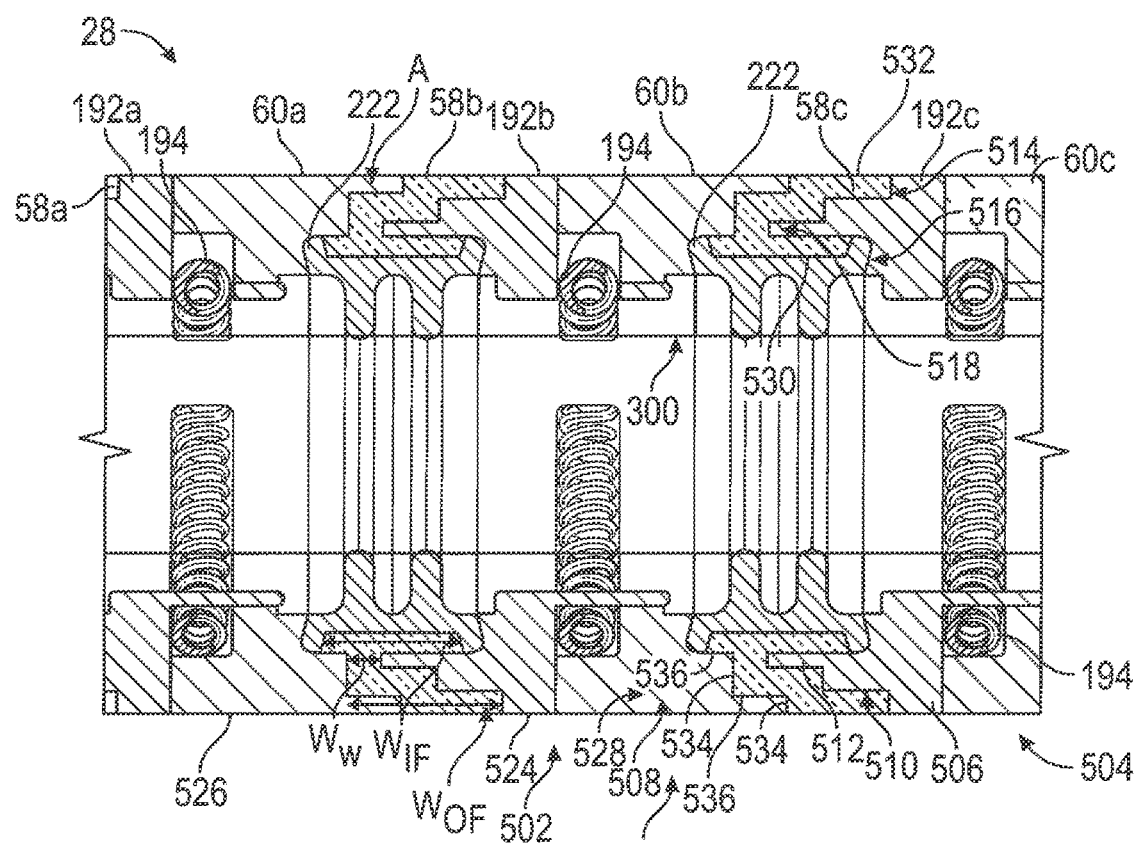
FIG. 20 is a view similar to that of FIG. 19, except reflecting a third embodiment of the reinforcement of the insulator rings.
Figure 21:
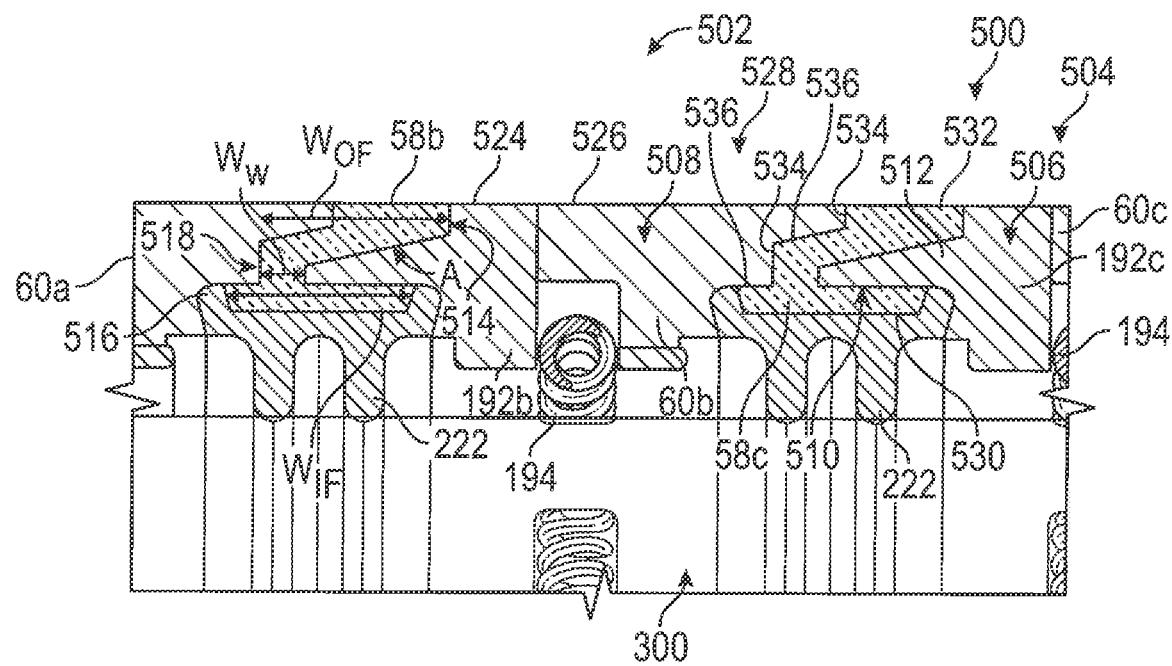
FIG. 21 is a view similar to that of FIG. 17, except reflecting a fourth embodiment of the reinforcement of the insulator rings.

The discussion now turns to FIGS. 17-21 for purposes of comparing four different embodiments of reinforced insulator rings 58a-58d. FIG. 17 is the same view as FIG. 9 and reflects a first embodiment of the reinforcement of the insulator rings 58a-58d as already discussed in detail above. FIG. 18 is a view similar to that of FIG. 7, except reflecting a second embodiment of the reinforcement of the insulator rings 58a-58d, and FIG. 19 is an enlarged view of a central portion of the connector assembly 28 depicted in FIG. 18. FIG. 20 is a view similar to that of FIG. 19, except reflecting a third embodiment of the reinforcement of the insulator rings 58a-58d, and FIG. 21 is a view similar to that of FIG. 17, except reflecting a fourth embodiment of the reinforcement of the insulator rings 58a-58d.

As can be understood from a comparison of the four embodiments reflected in FIGS. 17-21, each of the connector assemblies 28 has a shared configuration. Specifically, each of the connector assemblies 28 includes electrically insulative segments 500 and at least first and second electrically conductive segments 502, 504 axially spaced-apart (i.e., distally-proximally space-apart) from each other by the electrically insulative segments. Each electrically conductive segment 502, 504 includes a connector ring 60a-60c, a spring housing 192a-192c and a spring 194 supported by the spring housing. Each connector ring is in electrical communication with its respective and spring housing.

Each electrically insulative segment 500 includes an insulator ring 58a-58d that is positioned between a pair of electrically conductive segments 502, 504. Each insulator ring 58a-58d includes a first end 506 and a second end 508 axially (i.e., distally-proximally) opposite the first end. The first end 506 includes a first recess 510 that opens axially (i.e., distally-proximally) and receives therein a portion 512 of the first electrically conductive segment.

As can be understood from FIGS. 17-21, a spring 194 extends radially inward from each spring housing 192a-192c, and each spring housing contacts a respective connector ring 60a-60c. Each electrically insulative segment 500 also includes a seal ring 222 radially inward of each respective insulator ring 58a-58d.

For each of the embodiments depicted in FIGS. 17-21, the insulator ring 58a-58d includes a radially outer flange portion 514, a radially inner flange portion 516, and a web portion 518 radially extending between the radially outer flange portion and the radially inner flange portion. The web portion 518 has an axial (i.e., distal-proximal) width $W_W$ that is between approximately 10 percent to approximately 30 percent of the axial (i.e., distal-proximal) width $W_{OF}$ of the radially outer flange portion 514. The web portion 518 also has an axial (i.e., distal-proximal) width $W_W$ that is between approximately 20 percent to approximately 30 percent of the axial (i.e., distal-proximal) width $W_{IF}$ of the radially inner flange portion 516. In second embodiment of FIGS. 18-19, the web portion 518 of the insulator ring has an axial (i.e., distal-proximal) width $W_W$ of approximately 0.02 inch and the outer flange portion 514 has an axial (i.e., distal-proximal) width $W_{OF}$ of approximately 0.102 inch and an overall radial diameter of approximately 0.225 inch.

As can be understood from a review of each of the embodiments depicted in FIGS. 17-21, the reinforced configurations of the insulator ring 58a-58d provides the insulator rings with sufficient strength to resist deflection and failure when the header is injection molded about the connector assembly. Also, the tortuous and extended routes along the ends 506, 508 of the insulator rings 58a-58d reduces the chances that the injection molding material is able to pass between the ends of the insulator rings and the portions of the connector rings 60a-60, the spring housings 192a-192c, the connector block 56 and/or the entrance ring 62 abutting against and mating with the ends 506, 508 of the insulator rings.

As illustrated in FIGS. 17-19, in the first and second embodiments, the second end 508 of each insulator ring 58a-58d includes a second recess 520 that opens axially (i.e., distally-proximally) and receives therein a portion 522 of the second electrically conductive segment 504. For example, as is the case with the first embodiment of FIGS. 17-18, the connector ring 60a of the first electrically conductive segment 502 is the portion 512 of the first electrically conductive segment that is received in the first recess 510, and the connector ring 60b of the second electrically conductive segment 504 is the portion 522 of the second electrically conductive segment 504 that is received in the second recess 520. The first and second ends 506, 508 of the insulator ring 58a-58d are dissimilar in shape.

As another example and as is the case with the second embodiment of FIG. 19, the connector ring 60c of the first electrically conductive segment 504 is the portion 512 of the first electrically conductive segment that is received in the first recess 510, and the spring housing 192b of the second electrically conductive segment 502 is the portion 522 of the second electrically conductive segment that is received in the second recess 520. The first and second ends 506, 508 of the insulator ring 58a-58d are mirror images of each other.

As can be understood from FIGS. 17-19, for the recesses 510, 520 of each embodiment of the insulator ring, one recess opens distally axially the other recess will open proximally axially. Also, for each electrically conductive segment, a radially outermost circumferential surface 524 the spring housing is radially inward of a radially outermost circumferential surface 526 of the connector ring.

As illustrated in FIGS. 20-21, in the third and fourth embodiments, instead of a recess 510 like on the first end 506 of the insulator ring 58a-58d, the second end 508 of the insulator ring Includes a stepped configuration 528. The stepped configuration 528 extends radially outward from the inner flange portion 518 and axially towards the first end 506 from the second end 508.

As indicated in FIG. 20, for the third embodiment, the recess 510 also includes a stepped configuration. This stepped configuration of the recess 51 extends radially inward from the outer flange portion 514 and axially towards the second end 508 from the first end 506.

In the fourth embodiment and as can be understood from FIG. 21, the recess 510 tapers with respect to its radial height as it extends axially inwardly.

As reflected in the third and fourth embodiments of FIGS. 20 and 21, respectively, the radially inner flange portion 516 includes a radially inner circumferential surface 530 and the radially outer flange portion 514 includes a radially outer circumferential surface 532. The stepped configuration 528 includes at least two riser segments 534 and two tread segments 536 as the stepped configuration 528 extends between the radially inner circumferential surface 530 and the radially outer circumferential surface 532. There may be any number of risers and treads for the stepped configuration. For example, in some embodiments, there may be at least two riser segments or at least three riser segments. As indicated in FIG. 20 for the third embodiment, the riser segments each extend radially and the tread segments extend axially. As shown in FIG. 21 for the fourth embodiment, some of the tread segments may extend both axially and radially such that they are sloped. Some of the risers and treads may be considered to form part of the outer flange portion 514 such that they contribute to the width $W_{OF}$ of the radially outer flange portion 514. Also, one of the risers may form part of the web 516.

As Indicated by arrow A in the third and fourth embodiments of FIGS. 20 and 21, respectively, a portion of the insulator ring 58a-58d is radially sandwiched between a portion of the first electrically conductive segment and a portion of the second electrically conductive segment. Specifically, in some embodiments and as indicated by arrow A in FIGS. 20 and 21, a portion of the insulator ring 58a-58d is radially sandwiched between a portion of a spring housing 192a-192c and a portion of a connector ring 60a-60c on account of a longitudinal overlapping OL of portions of the connector ring 60a-60c and the spring housing 192a-192c. Depending on the embodiment, the overlap OL may be between approximately 0.0005 inch and approximately the entirety of the width $W_{OF}$ of the radially outer flange portion.

For the third and fourth embodiments and as indicated in FIGS. 20-21, a radially outermost circumferential surface 524 the spring housing 192a-192c is radially aligned with a radially outermost circumferential surface 526 of the connector ring 60a-60c.

For each of the embodiments depicted in FIGS. 17-21, the various components may be made of the same materials discussed above with respect to FIGS. 3-16, including MP35N or similar materials for the spring housings and the connector rings and polysulfone, PEEK or similar materials for the insulator ring.

Figure 22:
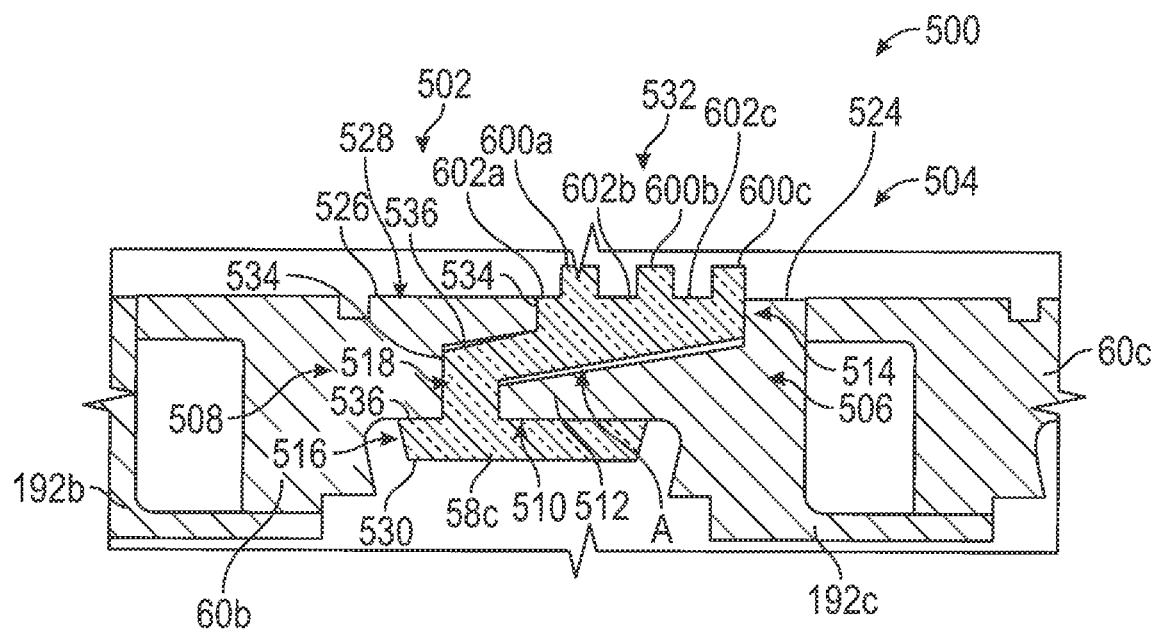
FIG. 22 is a view similar to that of FIG. 21 and illustrates that one or more of the insulator rings can have a ridged radially outer circumferential surface that provides reinforcement for the insulator ring and a greater electrical creepage length from metal contact to metal contact.

FIG. 22 illustrates an alternative embodiment of an insulator ring 58c similar to those discussed above with respect to FIG. 21, except the insulator ring 58c in FIG. 22 has a ridged radially outer circumferential surface 532. This ridged radially outer circumferential surface 532 provides reinforcement for the insulator ring 58c and an increased electrical creepage length from metal contact 60b to metal contact 192c. As shown in FIG. 22, the ridged radially outer circumferential surface 532 includes a number of radially outward extending ridges 600a, 600b, 600c that form circumferentially extending rings. These ridges 600a, 600b, 600c radially outwardly extend from, and are longitudinally separated by, recesses 602a, 602b, 602c that form circumferentially extending recesses.

Figure 23:
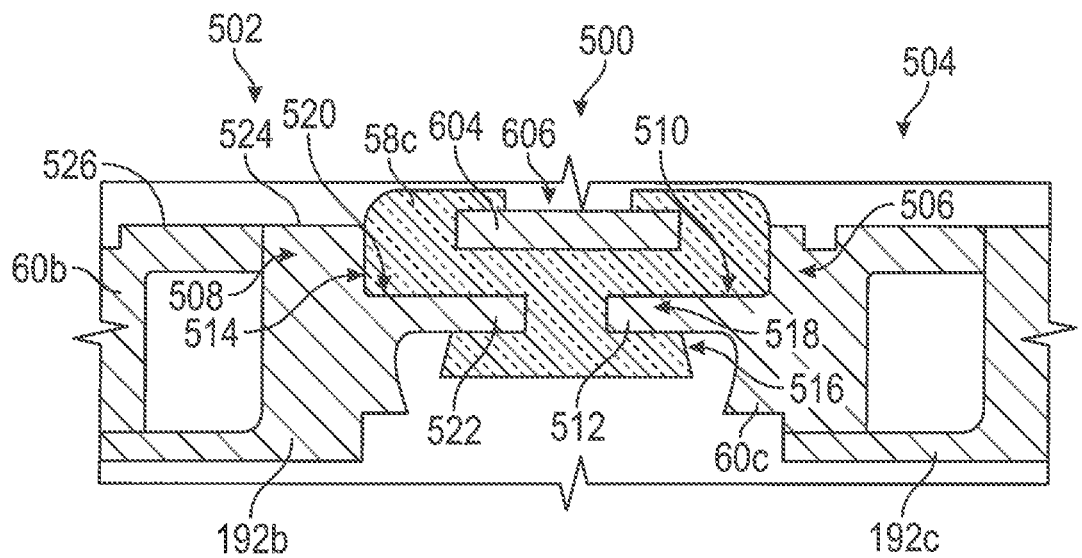
FIGS. 23 and 24 are views similar to that of FIG. 19 and Illustrate that one or more insulator rings can have a reinforcement ring in the radially outer flange portion of the insulator ring.
Figure 24:
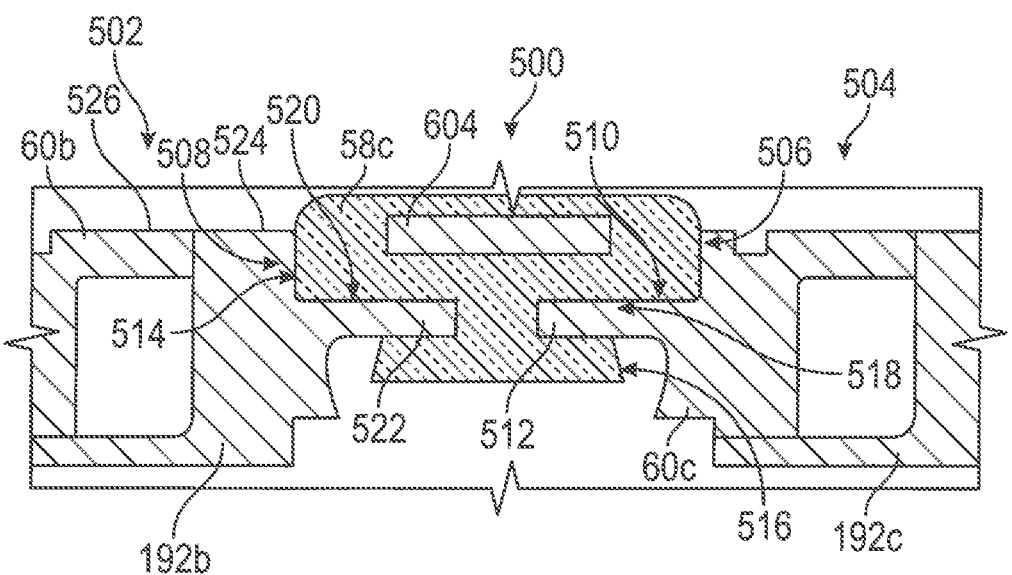

FIGS. 23 and 24 illustrate alternative embodiments of an insulator ring 58c similar to those discussed above with respect to FIG. 19, except the insulator rings 58c in FIGS. 23 and 24 have a reinforcement ring 604 in the radially outer flange portion 514. This reinforcement ring 604 may have a width approximately equal to that of the width $W_{IF}$ of the inner flange 516, as can be understood from a comparison of FIGS. 19, 23 and 24.

As indicated in FIG. 23, the reinforcement ring 604 may be radially outwardly exposed in the radially outer surface of the outer flange 514 due to a gap 606 defined in the radially outer surface of the outer flange. Alternatively and as illustrated in FIG. 24, the reinforcement ring 604 may be completely imbedded within the confines of the outer flange 514 where the flange 514 does not have the gap 606 defined therein.

As shown in FIGS. 23 and 24, the reinforcement ring 604 is centered distal-proximal over the center of the web 518 of the insulator ring 58c that occupies the gap between the portions 512, 522 of the first and second electrically conductive segments 502, 504. The reinforcement ring 604 overlaps not only the gap between the portions 512, 522 but also longitudinally overlaps a substantial part of each portion 512, 522 as overlaps OL. Depending on the embodiment, each overlap OL may be between approximately 0.0005 inch and approximately the entirety of the width $W_{OF}$ of the radially outer flange portion. As a result, a sandwiched and overlapping structural arrangement exists in the region of the gap between the portions 512, 522, as noted by each arrow A. Since the reinforcement ring 604 is made of MP35N, stainless steel or other materials that are substantially more resistant to flexing and failure and the reinforcement ring 604 extends over the gap between the portions 512, 522 and substantially overlaps the portions 512, 522, the insulator ring 58c is substantially reinforced to resist deflection and structural failure in the region it would most likely deflect or fail absent the reinforcement ring circumferentially extending along the circumferentially extending outer flange of the insulator ring.

The foregoing merely illustrates the principles of the various embodiments described in this disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. An implantable pulse generator for administering electrotherapy via an implantable lead, the pulse generator comprising:
   a housing; and
   a header connector assembly coupled with the housing and comprising a connector assembly and a header enclosing the connector assembly, the connector assembly comprising an electrically insulative segment, a first electrically conductive segment, and a second electrically conductive segment axially spaced apart from the first electrically conductive segment by the electrically insulative segment;

wherein each electrically conductive segment comprises a connector ring, a spring housing and a spring supported by the spring housing, each of the spring housing and the spring being retained, at least in part, within the connector ring, and the connector ring and spring housing being in electrical communication with each other and having outwardly projecting members; and wherein the electrically insulative segment comprises an insulator ring that is positioned between the first and second electrically conductive segments, the insulative segment comprising a first end and a second end axially opposite the first end, the first and second ends having inwardly sloping conical surfaces that abut the outwardly projecting members to resist radial inward movement of the insulative segment.

2. The implantable pulse generator of claim 1, wherein the insulator ring comprises a first end and a second end axially opposite the first end, the first end comprising a first recess that opens axially and receives therein a portion of the first electrically conductive segment and wherein the second end of the insulator ring comprises a second recess that opens axially and receives therein a portion of the second electrically conductive segment.

3. The implantable pulse generator of claim 2, wherein the connector ring of the first electrically conductive segment is the portion of the first electrically conductive segment that is received in the first recess, and the connector ring of the second electrically conductive segment is the portion of the second electrically conductive segment that is received in the second recess.

4. The implantable pulse generator of claim 2, wherein the connector ring of the first electrically conductive segment is the portion of the first electrically conductive segment that is received in the first recess, and the spring housing of the second electrically conductive segment is the portion of the second electrically conductive segment that is received in the second recess.

5. The implantable pulse generator of claim 4, wherein the first recess opens distally axially, and the second recess opens proximally axially.

6. The implantable pulse generator of claim 2, wherein the portion of the first electrically conductive segment is the corresponding spring housing, and the portion of the second electrically conductive segment is the corresponding connector ring.

7. The implantable pulse generator of claim 1, wherein the insulator ring comprises a radially outer flange portion, a radially inner flange portion, and a web portion radially extending between the radially outer flange portion and the radially inner flange portion.

8. The implantable pulse generator of claim 7, wherein the second end comprises a stepped configuration comprising a plurality of radially stepped surfaces extending inwardly from the radially outer flange portion.

9. The implantable pulse generator of claim 8, wherein the stepped configuration extends radially outward from the inner flange portion and axially towards the first end from the second end.

10. The implantable pulse generator of claim 8, wherein the first recess comprises a stepped configuration comprising a second plurality of radially stepped surfaces extending inwardly from the radially outer flange portion.

11. The implantable pulse generator of claim 10, wherein the stepped configuration of the first recess extends radially inward from the outer flange portion and axially towards the second end from the first end.

12. The implantable pulse generator of claim 8, wherein the radially inner flange portion comprises a radially inner circumferential surface and the radially outer flange portion comprises a radially outer circumferential surface, the stepped configuration comprising at least two riser segments and two tread segments as the stepped configuration extends between the radially inner circumferential surface and the radially outer circumferential surface.

13. The implantable pulse generator of claim 12, wherein the at least two riser segments each extend radially and the at least two tread segments extend axially.

14. The implantable pulse generator of claim 7, wherein insulator ring further comprises a reinforcement ring in the radially outer flange portion.

15. The implantable pulse generator of claim 14, wherein the reinforcement ring extends over the web portion.

16. The implantable pulse generator of claim 14, wherein the reinforcement ring longitudinally overlaps at least one of a portion of the first electrically conductive segment or a portion of the second electrically conductive segment.

17. The implantable pulse generator of claim 7, wherein the radially outer flange portion comprises radially outward extending ridges that form circumferentially extending rings.

18. The implantable pulse generator of claim 1, wherein a portion of the insulator ring is radially sandwiched between the portion of the first electrically conductive segment and a portion of the second electrically conductive segment.

19. The implantable pulse generator of claim 1, wherein the portion of the first electrically conductive segment and a portion of the second electrically conductive segment longitudinally overlap.

20. The implantable pulse generator of claim 1, wherein the spring extends radially inward from the spring housing.

21. The implantable pulse generator of claim 1, wherein a radially outermost circumferential surface of the spring housing is radially aligned with a radially outermost circumferential surface of the connector ring.

22. The implantable pulse generator of claim 1, wherein the spring housing is separate from and contacts the connector ring.

23. The implantable pulse generator of claim 1, wherein the electrically insulative segment further comprises a seal ring radially inward of the insulator ring, the seal ring including the first and second ends having inwardly sloping conical surfaces that abut the outwardly projecting members to resist radial inward movement of the seal ring and the insulator ring.

24. The implantable pulse generator of claim 23, wherein at least one of the connector ring and spring housing include the outwardly projecting members that about the inwardly sloping conical surfaces of the seal ring to resist the radial inward movement.

25. The implantable pulse generator of claim 1, wherein at least one of the connector ring and spring housing include the outwardly projecting members that about the inwardly sloping conical surfaces of the insulative segment to resist the radial inward movement.

26. The implantable pulse generator of claim 25, wherein the connector ring includes a first outwardly projecting member and the spring housing includes a second outwardly projecting member that abut the inwardly sloping conical surfaces of the first and second ends, respectively, to resist radial inward movement of the insulative segment.

* * * * *